US010386327B2

(12) United States Patent
Shachar

(10) Patent No.: US 10,386,327 B2
(45) Date of Patent: Aug. 20, 2019

(54) CARBON NANOTUBE BIOFET WITH A LOCAL AMPLIFIER IN A SYSTEM ARRAY FOR ANALYSIS OF BIOMARKERS AND METHOD OF ANALYSIS OF SAME

(71) Applicant: Sensor Kinesis Corporation, Los Angeles, CA (US)

(72) Inventor: Josh Shachar, Santa Monica, CA (US)

(73) Assignee: Sensor Kinesis Corporation, Los Angeles, CA (US)

( * ) Notice: Subject to any disclaimer, the term of this patent is extended or adjusted under 35 U.S.C. 154(b) by 178 days.

(21) Appl. No.: 15/724,908

(22) Filed: Oct. 4, 2017

(65) Prior Publication Data

US 2018/0038824 A1 Feb. 8, 2018

Related U.S. Application Data

(62) Division of application No. 14/625,445, filed on Feb. 18, 2015, now Pat. No. 9,810,661.

(51) Int. Cl.
*G01N 31/00* (2006.01)
*G01N 33/50* (2006.01)
*G01N 33/48* (2006.01)
*G01N 15/06* (2006.01)
*G01N 33/00* (2006.01)
*G01N 27/414* (2006.01)
(Continued)

(52) U.S. Cl.
CPC ..... *G01N 27/4145* (2013.01); *G01N 27/4146* (2013.01); *G01N 33/5438* (2013.01); *H01L 51/0049* (2013.01); *H01L 51/0558* (2013.01)

(58) Field of Classification Search
CPC ...... G01N 27/403; G01N 15/06; G01N 33/00; G01N 33/48; G01N 31/00; G01N 33/50
USPC ..... 422/68.1, 50, 82.01, 82.02; 436/43, 149; 977/700, 702, 705, 742, 953, 957, 958, 977/936, 938; 257/253; 702/1, 19, 22, 702/23, 27, 30
See application file for complete search history.

(56) References Cited

U.S. PATENT DOCUMENTS 4,072,576 A * 2/1978 Arwin ............... C12Q 1/001
  435/4
4,238,757 A * 12/1980 Schenck .......... G01N 33/54373
  257/253
(Continued)

*Primary Examiner* — Brian J. Sines
(74) *Attorney, Agent, or Firm* — Marcus C. Dawes; Daniel L. Dawes

(57) ABSTRACT

A bioFET cell for measuring a time dependent characteristic of an analyte bearing fluid includes a source, a drain, a semiconductive single wall carbon nanotube network layer extending between the source and drain electrodes and electrically coupled there between, a gate insulatively spaced from and disposed over and extending between the source and drain electrodes, a layer of at least one selected antibody disposed on and linked to the polymer layer to functionalize the semiconductive single wall carbon nanotube network layer to a selected target biomarker corresponding to the at least one selected antibody so that electron transport into the semiconductive single wall carbon nanotube network layer is facilitated, where the source, drain and gate electrodes with the carbon nanotube network layer form a defined channel through which the analyte bearing fluid may flow, and a high impedance source follower amplifier coupled to the source electrode.

3 Claims, 23 Drawing Sheets

(51) Int. Cl.
    *G01N 33/543*    (2006.01)
    *H01L 51/00*     (2006.01)
    *H01L 51/05*     (2006.01)

(56) References Cited

U.S. PATENT DOCUMENTS

| | | | | |
|---|---|---|---|---|
| 4,314,821 | A * | 2/1982 | Rice | G01N 29/036 310/312 |
| 4,444,892 | A * | 4/1984 | Malmros | C12Q 1/00 324/71.5 |
| 4,900,423 | A * | 2/1990 | Iida | C12Q 1/005 204/403.1 |
| 8,145,434 | B2 * | 3/2012 | Shachar | G01N 33/54373 702/19 |
| 2002/0127623 | A1 * | 9/2002 | Minshull | C12N 9/1252 435/7.92 |
| 2008/0231361 | A1 * | 9/2008 | Ludwig | B82Y 10/00 330/252 |
| 2010/0282617 | A1 * | 11/2010 | Rothberg | C12Q 1/6825 205/780.5 |
| 2014/0367750 | A1 * | 12/2014 | Fife | G01N 27/4148 257/253 |
| 2015/0064829 | A1 * | 3/2015 | Fife | G01N 27/414 438/49 |
| 2015/0125872 | A1 * | 5/2015 | Chen | G01N 33/54373 435/7.1 |
| 2017/0241943 | A1 * | 8/2017 | Rothberg | C12Q 1/6874 |

\* cited by examiner

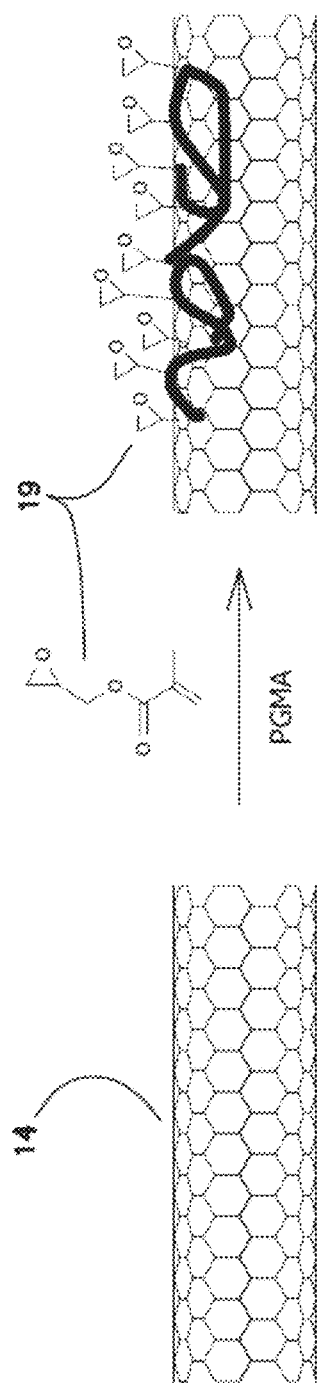
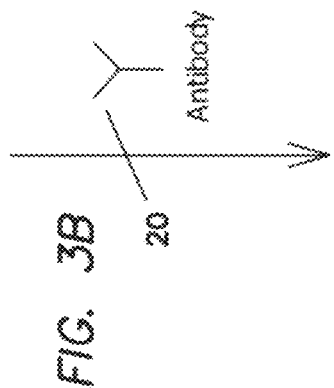
FIG. 3A Carbon nanotubes
FIG. 3B PGMA
FIG. 3C Antibody
FIG. 3D Biomarkers

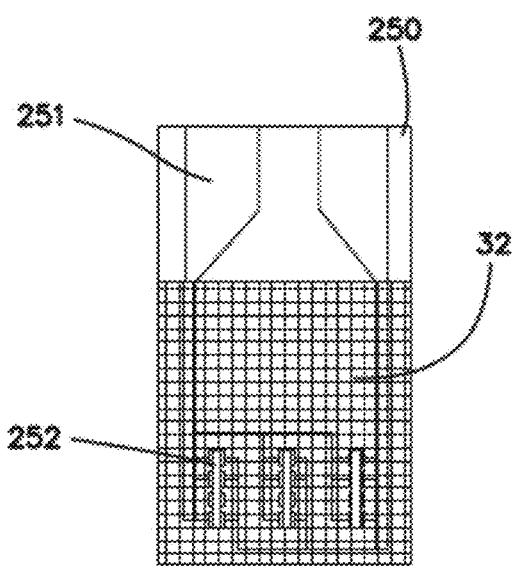 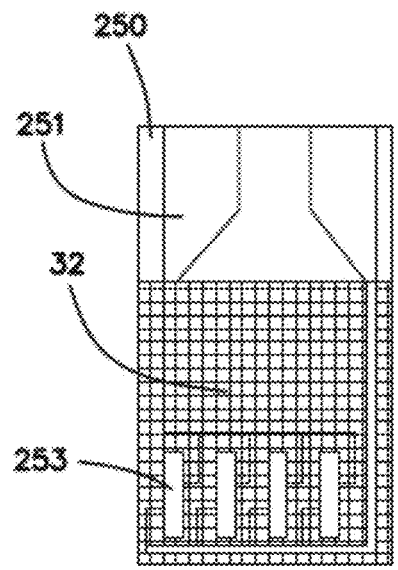
FIG. 6A          FIG. 6B
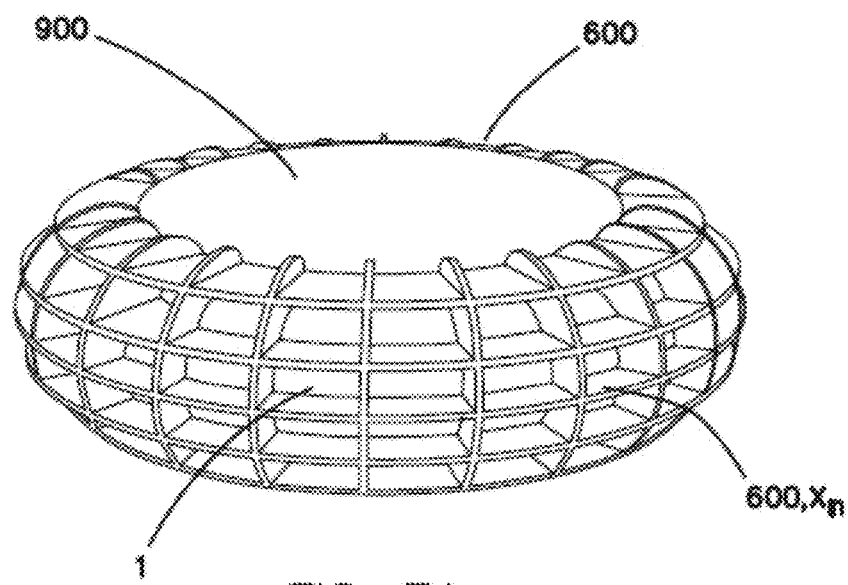
FIG. 7A

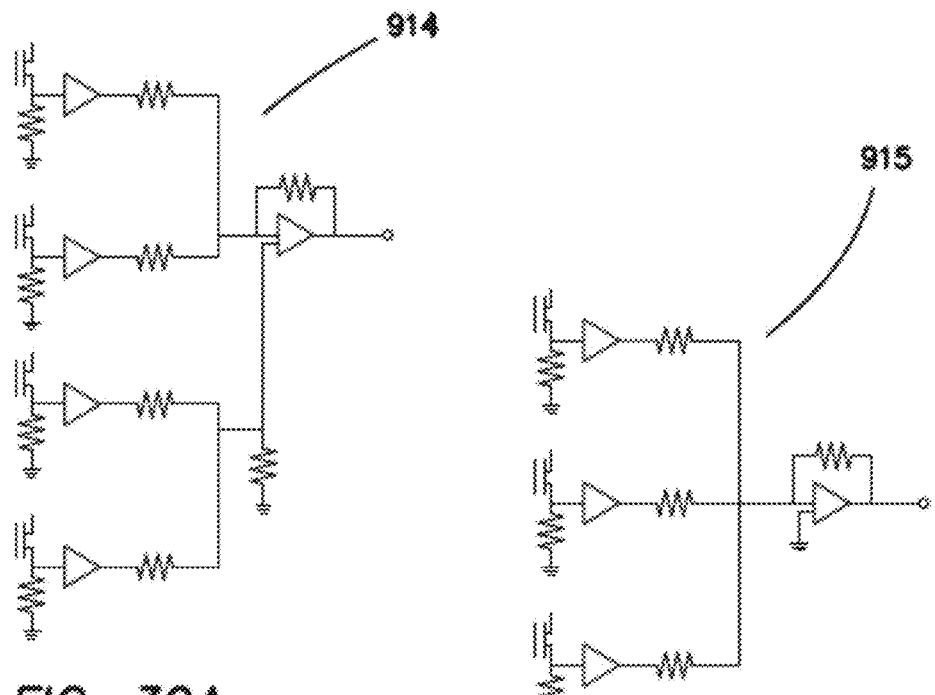
FIG. 30A
FIG. 30B
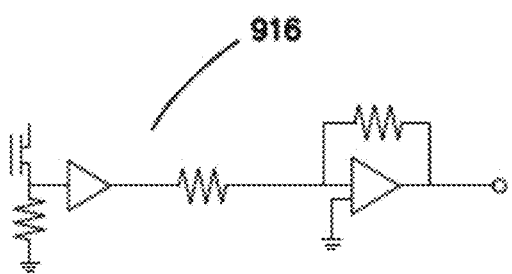
FIG. 30C
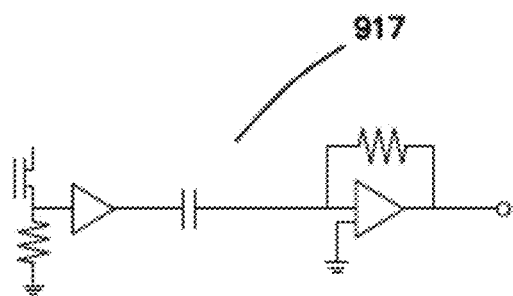
FIG. 30D

CARBON NANOTUBE BIOFET WITH A LOCAL AMPLIFIER IN A SYSTEM ARRAY FOR ANALYSIS OF BIOMARKERS AND METHOD OF ANALYSIS OF SAME

BACKGROUND OF THE INVENTION

Field of the Invention

The invention relates to the field of field effect transistors used as solid-state biosensors. More particularly, the invention is directed to a field effect transistor and arrays using the same in which the gate is acting as an "open base" with a fixed parallel plate of carbon nanotubes, which has been functionalized and which exhibits characteristics of ballistic transport (quantum tunneling) between the analyte and the antibody due to the hybridization process. G06F 11/00

Prior Art

"Method and Apparatus for Forming a Homeostatic Loop Employing an Aptamer Biosensor", U.S. Pat. No. 8,145,434, issued Mar. 27, 2012, hereby incorporated by reference in its entirety. Controlling the covalent bonding of antibodies onto functionalized carbon nanotubes using a single field effect transistor is a key step in the design and preparation of nanotube-based transducer for targeting cancer cells, biomarkers and synthetic oligonucleic acid or peptide. The chemical biosensors forming the bioFET architecture (cellular arrays) undergo electrical impedance (capacitive) changes due to hybridization of biomarkers which are realized on a scale of pico-amp increments.

Over the last decade, a variety of protein and DNA sensors have been developed circumventing the need for fluorescent labeling and optical imaging. Development of these label-free detection schemes is motivated by the need for faster, lower-cost detection of biomolecular agents. This access to quantitative information about the presence of specific bio-molecules in a patient's body or a pathogen in food or water is a critical step toward more accurate and personalized medical care as well as early detection of epidemiologic trends. To detect unlabeled bio-molecules, the label-free detection schemes utilize intrinsic protein properties such as polarizability, mass and electric charge, where a bioFET cell's reliance on the dielectric constant of bio-molecules changes the FET's gate characteristics and thus enable quantification of the hybridization process.

In the class of charge-sensitive biosensors, the use of semiconducting carbon nanotubes is extremely promising due to the electrical as well as the spatial properties of carbon nanotubes, as a mechanical scaffolding in support of the chemical linker and its antibody payloads, as well as the ballistic transfer characteristics of their hollow cylinders with their $sp^2$ bonding, which improve the device's characteristics.

Whereas a conventional field-effect transistor (FET) uses a gate contact to control the conductance of the semiconductor between its sources and drain contacts, the BioFET sensor array replaces the gate structure response, by the formation of a biofunctionalized layer of immobilized probes formed out of carbon nanotubes which act as surface receptors to attenuate the gate. When, a matching target molecule binds to the receptor, the charge distribution in the boundary layer at the liquid-transducer interface of the device changes. Hence this modulation of the conductance of the transducer by the selective specificity of the analyte binding to the antibody (the hybridization), results in an electrical detection of $V_{ds}$ verses $I_{ds}$, ($G_v$) by the bioFET gate structure, thereby improving the receptivity, gain, accuracy and repeatability of measurement by the device.

One of the drawbacks of the current state of the art is the inability of existing techniques to form an integrated apparatus that creates real time mimicry of the cellular biological processes of hybridization by the "sensor molecule", namely the molecule that selectively binds with a molecule whose concentration is to be measured in a sample. An example for such a sensor molecule may be an antibody, an antigen, a protein, a receptor, an aptamer, a peptide, a DNA strand, or an enzyme.

Biosensors which continuously monitor their surroundings to provide background statistics and warnings against unhealthy conditions are well known in the art of biosensors. There are numerous examples of gravimetric biosensors. The basis of detection is the decrease in the resonant frequency of a resonator that occurs as analyte species attaches to the resonating element. Analyte specificity is conferred for biological analytes by functionalizing the exposed surface of the gate and its conductance and its electrical resolution to enable a measurement that phenomenologically mimics the underlying biology.

For example Arwin, et al. U.S. Pat. No. 4,072,576 teaches a method for studying biochemical reactions in which a substance, whose activity or concentration is to be determined and where the affects a substrate specific for a biochemical reaction is measured. In many of the prior art applications the electrodes are coated with the substrate, determining a control value. The capacitance in a measuring device containing the electrodes is determined, the target substance is introduced into the measuring device, and the change in capacitance is measured, thereby obtaining a quantitative measure of the activity or concentration of the substance present in the sample affecting the specific substrate on the electrodes.

Conventional biosensors suffer from their inability to distinguish between like molecules and their timing of hybridization during the measurement process. In another class of biosensors the molecular interactions can be detected electronically through the polarizability of biological molecules' affinity, or optically through the use of fluorescence tags, radiometrically through the use of radioactive labeled tags, or acoustically. The use of labeling molecules is time consuming and requires many preparatory steps, which make the technique impractical in a disposable label free application.

Many variations on the theme of galvanometric and optically coupled biosensors where developed and their bases fundamentally follow the application of by Bergveld (1970) where the principle of the so-called "Ion Selective Field Effect Transistor", (ISFET) is the common thread. An example of such use is Schenck, U.S. Pat. No. 4,238,757 which describes a field effect transistor including a conventional source and drain electrodes which employs, in the gate region, a layer of an antibody specific to a particular antigen.

Rice U.S. Pat. No. 4,314,821 describes a method and kit for determining the total amount of an immunologically-reactive substance in a liquid sample containing interfering material capable of binding to an antigen. The method involves the steps of: contacting a liquid sample containing an antibody with the surface of a piezoelectric oscillator having a layer of antigen specific for the antibody attached thereto; washing and drying the oscillator; and measuring the resonance frequency of the oscillator.

Malmros, U.S. Pat. No. 4,444,892 introduces a sensor and semiconductor device for determining the concentration of an analyte in a medium. The device features an element constructed of semiconductive organic polymer associated with a binding substance having a specific affinity for the analyte.

Lida, et al. U.S. Pat. No. 4,900,423 discloses an enzyme sensor comprising an enzyme acting specifically on a substrate and a transducer for converting into an electrical signal the quantitative change of a substance or heat, which is produced or consumed during an enzyme reaction.

In another class of biosensor designed for optical surface plasmon resonance (SPR) detection of binding of a ligand-binding agent to the surface-bound ligand, the biosensor surface is a transparent dielectric substrate coated with a thin metal layer on which the monolayer is formed, where the substrate and metal layer form a plasmon resonance interface. The detector functions to excite surface plasmons, at a plasmon resonance angle that is dependent on the optical properties of the metal film and attached monolayer, and to detect the shift in plasmon resonance angle produced by binding of ligand binding agent to the ligand. As in the previous classes of available biosensor, the SPR apparatus is limited to laboratory setting with highly qualified individual to operate and assess the results obtained from the measurement. The use of biosensor designed for optical detection of binding of a ligand-binding agent to the surface bound ligand, and where the detector functions to irradiate the biosensor surface with a light beam, and detect a change in the optical properties of the surface layer, e.g., monolayer with embedded heterodimer, produced by binding of ligand binding agent to the ligand, suffer from the same limitations outlined above.

The problem which has not been solved by the prior art is how to reliably measure the degree and time sequencing of a plurality of biomarkers in a fluid in real time in such a way that the degree and time sequencing of the plurality of biomarkers in a live cell is mimicked and resolved.

SUMMARY OF THE INVENTION

The problem of how to reliably measure the degree and time sequencing of a plurality of biomarkers in a fluid in real time in such a way that the degree and time sequencing of the plurality of biomarkers in a live cell is mimicked and resolved is solved by providing a bioFET cell using functionalized single walled nanotubes with a local high impedance amplifier on the output of the bioFET. The bioFET cells are paired as sensor and reference cells in an array, which is coupled through an analog signal processing and computational front end circuit into a digital back end circuit which controls the frequency sweep cycling of the array, data storage and data processing of cell impedance magnitude and phase. A phase space density matrix of the plurality of biomarkers can thus be generated from which the diffusion equation of the corresponding underlying cellular biological activities of the corresponding plurality of biomarkers can be solved and statistical counting of hybridization of protein and analyte in real time achieved.

A solid-state biosensor for label-free detection of biomarkers such as; c-erbB-2, p53 and VEGF165 hybridization is presented. The apparatus is realized by forming a matrix-array of parallel field effect transistors (BioFET's) with a gate ("open base") exhibit improved device characteristics based on an integrated resistive/capacitive variable load of protein formed on a functionalized single walled carbon nanotube network coupled to a local source follower pre-amplifier. The apparatus allows the realization of an automated sampling device which enables a detection mechanism based on an electrochemical binding of circulating analytes with immobilized antibodies. The binding of these two molecules, antibody-antigen (Ab+Ag), modulates the threshold voltage of a circuit, while changing the impedance (capacitance) of the circuit. The circuit is further characterized by an electrode coded with a p-doped Si substrate, enhancing the affinity between the antibody molecules and the analytes.

The combined array of bioFET units integrally forming a fluid cell is configured to direct the flow the analyte samples onto the active surfaces of a plurality of bioFET cells. The array of parallel bioFET cells presents a capacitive load acting as a dynamic bias on the individual counter-electrodes. Analog front end circuitry enables an analog computational apparatus to measure the sensory output(s) continuously over the time and frequency domains, further enabling detection, analysis, and data-storage which in turn further enables reporting of biomarker hybridization measurements. Moreover, this bioFET detector array accurately measures a quantifiable rate of change of the analyte/molecules in vitro, providing real time-mimicry of the cellular biomarker(s) as well as variety of biological analytes.

The apparatus and method is further generalized to further enable the construction of an analog biological computing device. The present invention is directed to chemical biosensors with an architecture where each cell of the sensor's array, is formed as a field effect transistor with an "open base" (gate), fabricated out of a carbon nanotube network (CNT's) and where the junction gap of the open base is further enhanced with a source follower amplifier. The cellular network of BioFET transducers is further integrated to form an analog computational apparatus by the unique and novel application of the bioFET array as a fluidic-chamber.

The illustrated embodiment of this application shows that the charged bio-molecules can be detected by the use of a BioFET array coupled with an analog interface unit in a manner that efficiently and markedly improves the current art of counting and identifying the sequencing of. stochastic biological events, where the need to identify the timing and location, including statistical measures of hybridization, is essential in uncovering the nature and specificity of cascading effects of protein sequences. (including the uncovering of statistical causal correlations of the different antibodies and their respective antigens)

The electrical as well as its geometrical (three dimensional layout) of the carbon nanotubes form the effective sensory area of the bioFET cell unit, coupled with the fact that typical diameter of individual members of CNT is in the order of 1-2 nm in diameter, enabling most of the atoms of the carbon nanotube to lay on a surface which functionally generates a carrier with exceptionally high electrical mobility. The $sp^2$ bonded carbon lattice is extremely stable in biological environments, and therefore provides for a practical substrate for the formation of biochemical links to an electronic device.

This application employs the data generated by measurements conducted on sample protein, for example VEGF165, to demonstrate the effective use of the apparatus and its method of detection, including calculating as well as reporting of the results of hybridization in a manner that is not being observed by the existing art.

The process the proposed apparatus employs the sensor molecule (analyte antibody combination) as the biasing element when attached to the substrate-dielectric of the FET. The gate geometry and its charge surrounding the channel of the FET is changed due to hybridization. This change in charge causes the conductance (G) of the FET channel to shift and which is therefore registered by the analog front circuitry. When the FET biosensor is biased in the sub-threshold region, (a critical parameter dependent on the geometry and metric of the gate design), a linear change in the charge transferred from target molecules to the sensor molecules surrounding the FET nano-channel occur, thereby causing a logarithmic change in the conductance of the FET nano-channel.

The cellular array of bioFET's is further enhanced by the analog circuitry and a digital processing unit. As illustrated below the analog computation is significantly more efficient in its use of resources than deterministic digital computation.

The aim of the inventive step in this application is to develop a method and implement it with an apparatus to enable counting the stochastic (non-linear events) and measurement of biological process to follow the evolution of hybridization of, for example, a biological molecule such as $VEGF_{165}$-biomarker, including the mimicking of the diffusion model of proteins by using the apparatus to account for the Boltzmann exponential laws of thermodynamics and by similar logarithmic electrochemical potentials occurring during the biological process of hybridization.

The method and this exemplary application of such "effective procedure" for the tracking and mimicking of biological processes, is centered on the use of a bioFET cell unit with the operators of summing, subtracting, integrating and differentiating the outputs available from the array of bioFET matrix using the analog computation unit with the cellular array of the bioFET sensor.

The present disclosure describes an apparatus that allows for architecture of a solid-state biosensor (bioFET) with local source follower amplifier for label-free detection of biomarker hybridization.

In one embodiment, the device is realized by forming a matrix array of bioFETs acting as parallel capacitors which forms the electrical configuration of the source, drain and gate, where the capacitive cell is a hybrid of semiconductive single-walled carbon nanotubes providing a resistive/capacitive load to an integrated local amplifier to achieve a high ratio of output signal to the lowest minimal electrochemical variations. This feature of the novel bioFET cell, allows a realization of low cost, portable biosensor apparatus, as a fully integrated device for detecting, measuring and computing the relevant parameters.

The present disclosure is directed to a biosensor in the form of a bioFET cell array and, more particularly, includes a plurality of outputs of a capacitive array of an integrated platform of bioFETs. It is fabricated using solid state techniques in conjunction with an oligonucleotide element, such as aptamers (oligonucleotide ligands that are selected for high-affinity binding to molecular targets), or alternatively an improved antibody described by the use of a half antibody which provides a dielectric differentiation due to the hybridization surface of the capacitor plates nested between the source and the drain of the bioFET cell.

In one embodiment the proposed invention aims to support a diagnostic measure, to emulate the growth rate of tumor development as a function of its analyte level in the bioFET sensing area chamber (effective geometry), while measuring the binding rate of the analyte molecules to the capacitor plate. The ability of the proposed apparatus to mimic the vectorial trends of tumor's biomarker(s) binding rate of analyte(s) molecules (biomarkers) is simulated by the equivalent circuit of the apparatus, and further provides an effective tool for recoding biological sequences, thereby enabling a means for reproducing them. The bioFET capacitive load added through the hybridization is then calculated and gives an accurate measure for the state of the system in question.

In one example of the apparatus, the bioFET cell(s) detect the presence of the VEGF165 molecules by the use of mechanism based on an electrochemical binding of an aptamer/antibody suitable to bind to such analyte.

In one embodiment of this application, we employ an example of a biomarkers used by the bioFET cellular array, using vascular endothelial growth factor, (VEGF165) which plays a critical role during normal angiogenesis and also in the pathological angiogenesis that occurs in a number of diseases, including cancer.

Initial attempts to block VEGF by using a sensory apparatus are limited by the complexity and length of processing times associated with the current art. The use of the apparatus to detect the humanized monoclonal antibody bevacizumab (Avastin, Genentech/Roche), and two kinase inhibitors sorafenib (Nexavar; Bayer) and sunitinib (Sutent, Pfizer) which target the VEGF receptor (VEGFR) tyrosine kinases is essential, since such steps are beginning to show promise in human cancer patients, including the ability to optimize VEGF blockade. Therefore, a portable in vitro or in-vivo device that accurately provides real-time feedback on VEGF levels is able to regulate, attenuate or modify the intake of anti-angiogenic-agents is crucial for any finely tuned anti-angiogenesis therapy.

The presently described system is capable of measuring VEGF levels by emulating the process where VEGF molecules binds to an immobilized VEGF aptamer antibody within a known time domain, providing an appropriate feedback based on the VEGF level in any regulated diagnostic and or therapeutic procedure where such a measure is used for treating malignancy.

In this application we employ the example of interactions between VEGF protein and their receptors as the respective binding of the aptamers or antibody and the VEGF receptor within the controlled conditions in the apparatus chamber, and demonstrate the effective use of such embodiment and its usefulness relative to the prior art. Details of signaling events and their biological outcome are concisely illustrated by simulating the binding rate of the VEGF molecule-binding to the aptamer or its antibody present in the proposed apparatus' chamber; hence, such parallel process of detecting as well as counting of such biological processes, provides the necessary quantitative trends and concentration values in the equivalent circuit of the apparatus.

In one and more embodiments of this application, we describe the fabrication of the proposed VEGF detector, using the improvements made in technique and equipment for fabricating miniature devices such as the geometry of the bioFET and its ancillary analog front-end or its hybrid digital module, and consequently, the improvements in silicon manufacturing and high-precision micro-electromechanical systems (MEMS), which enable fabrication of such an apparatus.

In another embodiment, the bioFET cell has an electrical polarity seeding, to naturally attract the intrinsically negative electric charge of VEGF molecules, while further modulating the threshold voltage of the circuit.

In another embodiment, the electrical polarity can be modulated to attract and then release the VEGF molecules to prevent a buildup of VEGF molecules on the sensor surface (the layering of carbon nanotubes between the source and the drain electrode) while preventing sedimentation and nonspecific bindings of ionic residue within the buffer solution, thereby enabling a continuous flow of biological fluids flowing through the bioFET chamber(s).

In another embodiment the bioFET is constructed with an electrode preferably coded with a p-doped Si substrate to enhance the affinity between the VEGF molecules and the antibody or aptamers causing the change in the impedance (due to capacitance loading) of the circuit containing the bioFET cell array. The array is configured to provide an unobstructed flow of the VEGF samples on the active surface of the chip, due to its use of the gate geometry and its metrics.

In one embodiment of the bioFET cell, the cellular array is formed with the option that one or more of the units are operating as an ISFET, where the gate voltage, $V_G$, is applied by a reference electrode (e.g., Ag/AgCl electrode), hence, fixing the potential of the test solution (analyte). When a sufficiently positive bias potential is applied to the gate (with respect to the bulk silicon substrate), an n-type inversion layer is induced in the channel between source and drain. The magnitude of the drain current, $I_D$, is determined by the effective electrical resistance of the surface inversion layer and the voltage, $V_{DS}$, (applied between source and drain). The operation of the ISFET is described by the processes (charge carrier distribution) which take place in each phase and at the interfaces, correspondingly, the drain current of the ISFET, $I_D$, is reduced from those parameters and conditions.

In one embodiment the device can be formed as an array of parallel capacitors which act as integrated, individual counter-electrode. The device is further equipped with a computational apparatus to render the sensory outputs over the time domain, resulting in detection of the analytic data of specific hybridization with its time stamps. This feature arises from the signal fidelity provided by employing a source follower amplifier. The apparatus is further integrated with A/D converter, resulting in a computation device based on a sampling algorithm for reporting on the statistical slices of time domain activity as well as the frequency domain changes due to the hybridization process.

In another embodiment, the device can provide an accurately measured and quantifiable rate of change of VEGF molecules in-vivo and enables improved diagnosis of tumor markers. As a result of such information (VEGF level and vectorial trends), the device with its auxiliary circuit improves the diagnostic capability of the medical staff in providing an early detection of minute changes of a quantifiable biomarkers within the blood, hence improving the odds of therapeutic outcome by providing base statistics, without the lengthy and expensive labeling techniques known in the art as enzyme-linked immunosorbent assay (ELISA).

In one embodiment of the proposed biosensor, the immobilized binding group is located in one or more areas on the surface of a membrane whose locations on the membrane, sizes and area immobilization densities are designed to maximize the observed frequency and/or amplitude shifts in the target analyte binding and to maximize the discrimination between all combinations of specific and non-specific binding. This discrimination may take three forms: (a) change in resonant frequency of the effective area formed on the CNT's with the immobilized chemical linker, (b) appearance or disappearance of a higher order harmonic shift, or (c) change in amplitude decay rates, a process detected by the analog front end of the proposed apparatus. In such a biosensor (a unit cell comprised of a bioFET is alternatively be loaded with plurality of antibody/antigen), a single array of bioFET units may be comprised of a plurality of individually addressable elements for actuation and for sensing purposes, as well as comparative measure relative to timing and density of processes occurring within the cells. This technique permits the specific measure of the sequencing order(s) of selected modes and enables simultaneous actuation of an alarm circuit or like devices. The principles of measuring biological cascading effects (of multiple proteins within the analyte), is essential parameter in uncovering the interdependence of causal statistics in the relation between the different biological species available in the analyte simultaneously.

In one embodiment, a simple and robust, as well as reversible method is provided which can reliably detect in one operation an analyte molecule.

An object may be achieved according to at least one embodiment of the invention by a binding of specified analytes in a sequence of method steps by using the bioFET cell.

In at least one embodiment, measurement is carried out in each case after the antibody is bound to circulating analytes, and its electrical value is counted in the time domain, stored, and reported.

At least one device for monitoring and controlling the hybridization of, for example, VEGF molecules over the matrix array positions of the chip and one device for controlling the rate of liquid flow in the associated detection device are present in the embodiment of the proposed apparatus. For this purpose, the sensor chip can be connected to a microfluidic system including precision pump.

Various embodiments relate to signal amplification methods for multiple biological assays, where the bioFET cell or its array in optional geometric configurations is electrically connected to a source follower amplifier (SFA). In general, biological target complexes are tagged by a seed substance that can catalyze the formation of a surface-enhanced substrate such as aptamers or antibody. The target complexes can then bind to capture reagents which include a VEGF molecule for example. The hybridized substrate is then generated on the seed substance through reduction of immobilized VEGF aptamer (Macugen). The target signals are detected by Pegaptanib, (an aptamer, a pegylated modified oligonucleotide, which adopts a three-dimensional conformation that enables it to bind to extracellular VEGF in an in vitro testing conditions, and Pegaptanib which specifically binds to the major pathological VEGF 165 isoform).

Accordingly, in one embodiment, a biological target complex including a target analyte associated with a first specific binding member is provided. The target complex further includes a second specific binding member that binds to the first specific binding member forming a target complex. The second specific binding member includes a seed particle suitable for catalyzing the formation of a surface-enhanced aptamer or antibody such as a VEGF. Subsequently, the complex substrate can be activated by means of the electronic circuit to provide the necessary change in impedance.

In one aspect, the invention includes a bioFET sensor apparatus emulating a binding event between a ligand and ligand-binding agent. The apparatus has a bioFET surface composed of carbon nanotubes (SWCNT) and chemical linker suitable for the targeted molecule(s), and two-subunit heterodimer complexes carried on the surface. The complexes are composed of a first and second, preferably oppositely-charged, peptides that together form a α-helical coiled-coil heterodimer. The first peptide is attached to the bioFET surface, and a ligand is covalently attached to the second peptide, accessible for binding by a ligand-binding agent. Binding of an anti-ligand agent to the ligand is detected by the bioFET array and the signal is enhanced by the electronic circuit such as a source follower amplifier.

In one general embodiment, the bioFET surface includes a monolayer composed of semi-conductive single-walled carbon nanotube chains anchored at their proximal ends to the bioFET surface, and having free distal ends defining an exposed monolayer surface. The heterodimer complexes in this embodiment are preferably embedded in the monolayer with chemical linker as it is shown in the drawings describing the bioFET construction and its topology, and the ligands are disposed on or near the monolayer surface. The monolayer may be formed alternatively on a metal, e.g., gold film, and may be composed of carbon nanotube chains attached at their proximal ends to the bioFET surface by a thiol linkage.

In one embodiment, the proposed apparatus contains a chamber which is adapted to contain an aqueous solution of redox species in contact with the monolayer, and the detector includes a circuit for measuring ion-mediated current across the monolayer, in response to binding events occurring between the receptor and ligand.

More generally, the invention provides a method of constructing an array of different, selected biological reagents attached to different, selected regions on an assay support surface comprising of the bioFET source, drain and gate with its novel geometry forming the internal chamber(s) as the flow cavity.

In one embodiment a micro-machined or printable structure (cavity), is generally formed using a semiconductor substrate such as a silicon wafer. One of the objects of the present invention is to realize further reduction in cost by integrating a minute structure and a semiconductor element controlling the minute structure over one insulating surface in one step. A minute structure has a structure in which a first layer formed into a frame-shape is provided over an insulating surface, a space being formed inside the frame, and a second layer is formed over the first layer. Such a minute structure and a thin film transistor can be integrated on one insulating surface in one step.

Further improvements of the device are illustrated by the architecture of the BioFET, where the hybrid construction of the substrate and its geometry (the transistor gate) with its "open base" are formed to enable a transduction of the hybridization between the antibody and the analyte, while mimicking the biological process dynamics is realized by the cavity geometry and the electrical characteristics of the bioFET.

In one embodiment the BioFET is constructed as an independent cell out of an active array of elements in the form of a matrix, resulting in an effective analog computation device, where each of the cell unit reports to a resident microcontroller the event activity and is summed, integrated or undergoes the process of measurement and counting via the arithmetical of the proposed apparatus.

The aim of the apparatus is to measure and mimic the hybridization process between antibody(s) and analyte(s) by further providing a means for counting/measuring such processes while emulating biological kinetics' process with mathematical analogues such as known in the art as: counting, summation, integration and differentiation.

The proposed device, utilizing nano-scale carbon nanotubes with their semiconductive electrical characteristics, improves the circuit detection for the following reasons: carbon nanotube-sized compatibility of the sensor's effective geometry enables the formation of FET devices with conducting channels on-demand. These features will become clear in the preferred embodiments demonstrating the use of biosensing and detection due to the unique architecture which enhances the detection and ease of fabrication of such a transistor with its "open base" geometry and the exponential increase of the surface area of the "open base" with its carbon nanotube construction.

Some embodiments of the application demonstrate the advantages of the BioFET architecture compared to the traditional optical methods as well as existing field effect transistor (FET), where a direct, label-free, (near) real-time, continuous signal is obtained, and where highly selective sensing is used followed by the binding between an antibody and an antigen, forming a specificity with resolution and accuracy which improves the current art. The above state of improved device characteristics (DC) is due to its higher surface-to-volume ratio and thus an increased modulation of the conductance by the bio-molecules. A concentration dependent increase in the source-drain current is observed in the regime of clinical significance, with a detection limit of approximately 30 fM (450 pg) observed and where the proposed apparatus was tested and reported an experimental data with resolution (using the bioFET unit) of concentration of $VEGF_{165}$ molecular with average molecular weight of 35 kDa.

In one embodiment the proposed device, utilizing nanoscale carbon nanotubes with their semiconductive electrical characteristics, improves the circuit detection for the following reasons: carbon nanotube-sized compatibility of the sensor's effective geometry enables the formation of FET devices with conducting channels on-demand.

In one embodiment of this application, the surface area of the "open base" of a BioFET minimizes the required analyte concentration, hence reducing the interface exchange hybridization. Due to such construction, the device characteristics (DC) offer an order of magnitude increase of analyte/antibody statistics of covalent matching and where the BioFET cell sensors benefit from further miniaturization, and increased detection rate. The improvements in DC are due to the FET-like construction of the source-drain and gate topology and material, which enables sensing protein-protein interactions, and protein interaction mechanisms. These improvements are due not only to the sheer fact of the device characteristics of real-time and a label-free detection, but also to its high sensitivity and selectivity, whereas the "open base" geometry increases mobility and facilitates transportation by improving the spatial opportunity access of the analyte and its antibody as the assay travels through the bioFET internal chamber. The statistical indices of accelerated hybridization are due to the electrical design of the gate, which further increases propulsion of antibody/antigen, due to molecular affinity of the cytoskeleton specificity of the analyte and the antibody.

In one embodiment the topological layout of the BioFET gate is described where the gate is placed on top of the source-drain structure to form a flow chamber geometry and where increase in conductance (G) of the hybridization kinetics process (the transduction between the analyte and the antibody exchange) is improved in semiconductive single-walled carbon nanotubes forming the "open base".

In one embodiment the carbon nanotubes collection (CNT's) which forms the "open base" are quantized (due to their one dimensionality and its limited number of allowed electronic states), and where the nanotubes behave consequently as quantum wires and charge carriers are transmitted through discrete conduction channels. This conduction mechanism is ballistic in nature and the electrons travel through the nanotubes channel without experiencing scattering, and as a result of tunneling, the electrons encounter no resistance and no energy dissipation in the conduction channel, leading to an improved phase relation between $V_{ds}$ and $I_{ds}$ curves, thereby reducing "noise" due to scattering effect on conduction, further improving the predictability of the device characteristics vs. the time constant evolution. Curve fitting and threshold voltage is adjustable by changing the diameter of the carbon nanotubes, hence the scalability of the bioFET to meet variety of protein molecular weights and electrical affinity-site detection geometries.

These and other features of the illustrated BioFET enable an accurate, near real-time computation of the data generated by the transducer action of the bioFET cell and its peripheral electronics, to define the time constant $\tau$ (tau) of the measured process. This embodiment is enhanced by high sampling rate by the use of a resident microcontroller, achieving an accurate and consistent count of hybridization rate on a scale consistent with medical diagnostic values having a resolution of 1 pg/mL (3.671 pmol/L), while measuring the analyte flow through the bioFET.

Many studies outlining the quantitative correlation of serum levels and tumor expression of vascular endothelial growth factor (VEGF) in patients indicate that those serum levels of VEGF may provide useful prognostic information in patients with various types of cancers. The ability to measure such vectorial expression can provide a prognostic as well as therapeutic tool in the hands of the physician (oncologist). To enable such resolution and accuracy of the measuring apparatus, it must be capable of resolving the process of hybridization product with magnitude of 40 pg/mL minimum, to achieve the degree of statistical confidence required.

The application with its preferred embodiment demonstrates that single channel field effect transistors (FET) incorporated as part of a device with network conducting channels using the functionalized carbon nanotube chemistry, provides a substantial improvement in comparison with the prior art.

In one embodiment of this application, the operation of the BioFET in a conducting buffer and in a dry environment demonstrate that the device characteristics improve the relation between $V_{ds}$-$I_{ds}$ output. The FET carbon nanotube "open base" construction, readily responds to changes in the local environment. Such effects have been examined by the inventor, when testing the BioFET using VEGF 165 molecules and linker using coating layers functionalized with poly(glycidyl methacrylate) (PGMA) with its specific properties of adhesion. The results of the use of this embodiment are illustrated by an example in this application.

In one embodiment the BioFET topology enables reduction in variation between the different devices fabrication due to the ease in a one step production technique, associated with the construction and functionalization of the BioFET's chemistry.

In one embodiment, the apparatus addresses the problem of biomolecular time-scale, which undergoes a variety of fluctuations and conformational changes that span several orders of magnitude.

In one embodiment of this application we highlight the usefulness of the method and apparatus described in processes involving VEGF, and Flk-1/KDR RTK, a process which has been implicated as the key endothelial cell-specific factor signaling pathway required for pathological angiogenesis-including tumor neovascularization, which in some therapeutic applications inhibits the VEGF tyrosine kinase signaling pathway, blocks new blood vessel formation in growing tumors, thereby leading to stasis or regression of tumor growth. Advances in understanding the biology of angiogenesis have led to the development of several therapeutic modalities for the inhibition of the VEGF tyrosine kinase signaling pathway. A number of these modalities are under investigation in clinical studies to evaluate their potential to treat various forms of human cancer, but the ability of such studies are limited by the fact that local, real-time in vivo measurement of the VEGF level and the trends of the VEGF transduction are not readily available. This and other biological processes can be improved by employing the proposed method and its implementation, by using the apparatus outlined by this application, whereby the sequencing and their time stamps can be emulated by the proposed apparatus. In tumor progression, activation of VEGF pathways promotes tumor vascularization, facilitating tumor growth and metastasis. Abnormal VEGF function is also associated with other diseases including atherosclerosis, psoriasis, age-related macular degeneration, diabetic blindness, rheumatoid arthritis, and hyperthyroidism. The members of the VEGF and VEGF-receptor protein families have distinct but overlapping ligand-receptor specificities, cell-type expression, and function. VEGF receptor activation in turn regulates a network of signaling processes in the body that promote endothelial cell growth, migration, and survival. It is clear that the ability of any apparatus to differentiate between such a complex assays, requires an apparatus that can emulate and mimic the stochastic-statistical hybridization of the protein and their sequences, a task that this application addresses.

These and other objects and features of the invention will become more fully apparent when the following detailed description of the invention is read in conjunction with the accompanying drawings.

BRIEF DESCRIPTION OF THE DRAWINGS

The following description of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

The accompanying drawings in which like reference numerals refer to identical or functionally-similar elements throughout the separate views and which are incorporated in and form part of the specification, further illustrate the present invention and together with the detailed description of the invention, serve to explain the principles of the present invention.

FIGS. 3A-3D are diagrams of the process of antibody attachment onto the surface of carbon nanotubes and capture of corresponding biomarkers.

FIGS. 6A and 6B are possible geometric layouts of the array of sensors: in FIG. 6A is a example of a 3×4 array of cells and in FIG. 6b there is a 4×1 array of cells although the number of sensors and number of columns can be chosen in any geometric arrangement as may be desired.

7A is a perspective view of a scaffold for an array of cells in the form of a torus.

Figure 8:
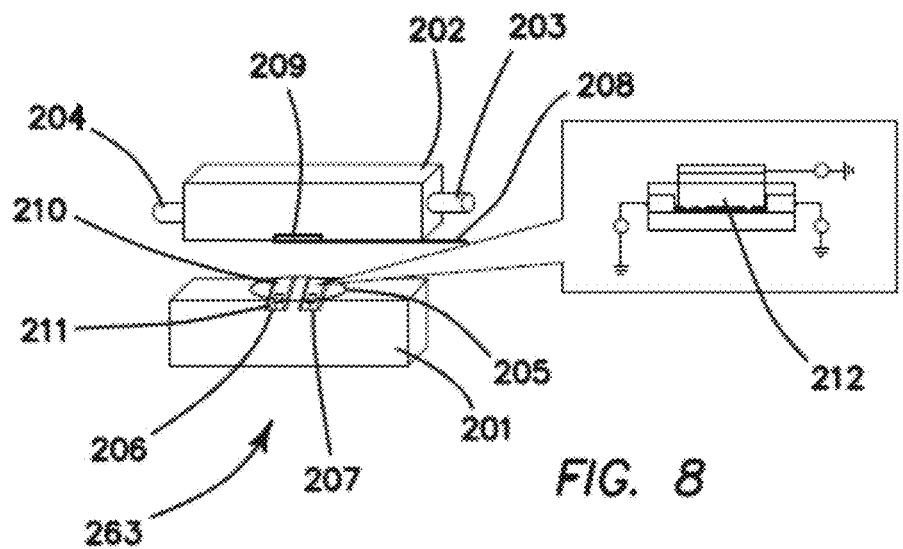

FIG. 8 is a diagram of a fluid flow cell including a sensor cell and corresponding reference cell pair.

Figure 9:
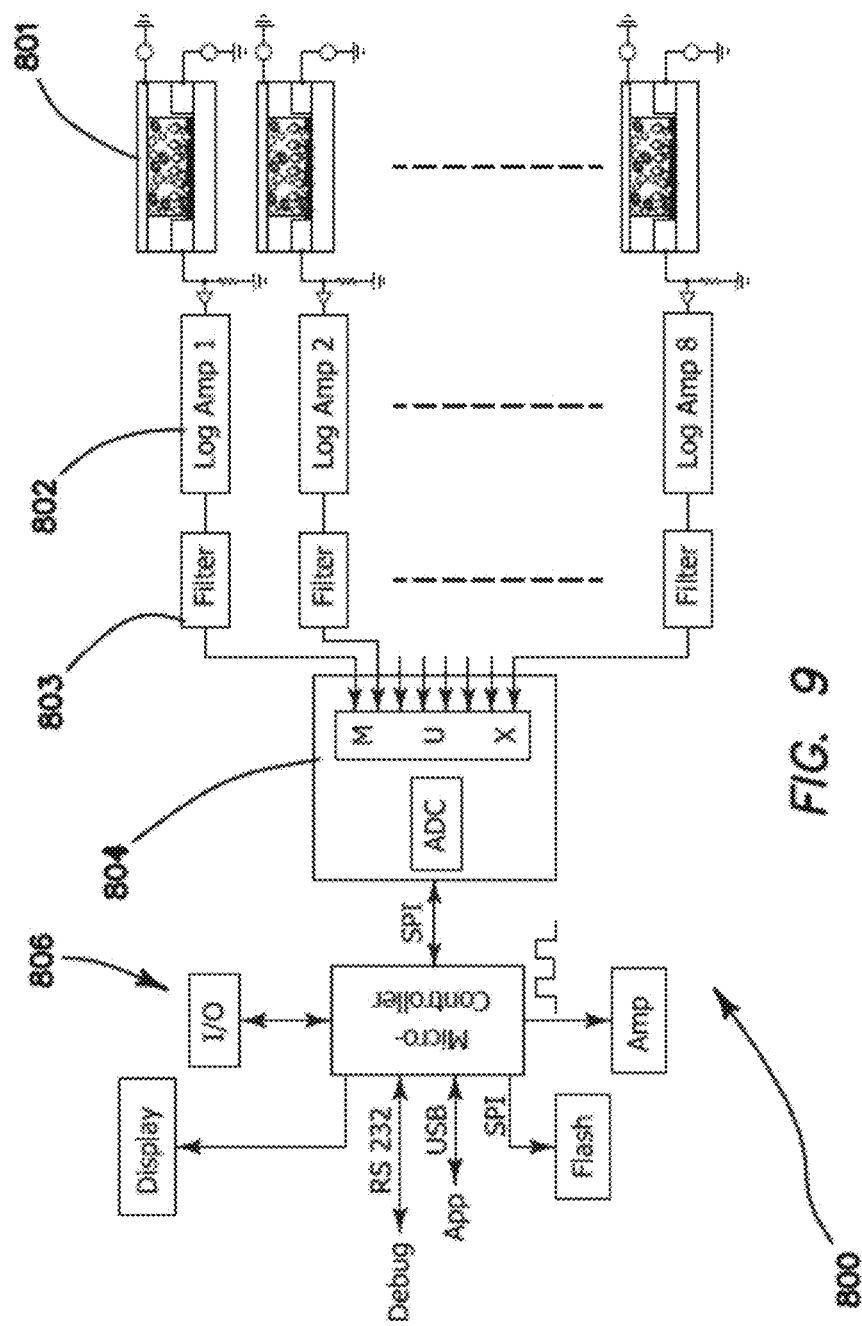

FIG. 9 is a block diagram of a pathfinder/reader describing the analog front end coupled to the array of cells which are multiplexed and digitized into a digital microcontroller.

Figure 10:
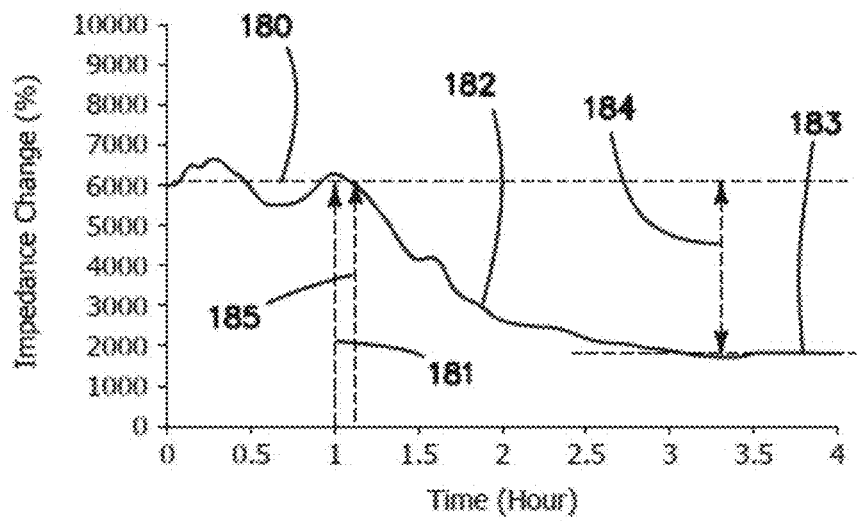

FIG. 10 is a graph of the impedance change in a cell as a function of time of the VEGF 165 (5000 pg/mL) at 1000 Hz in a model solution.

Figure 11:
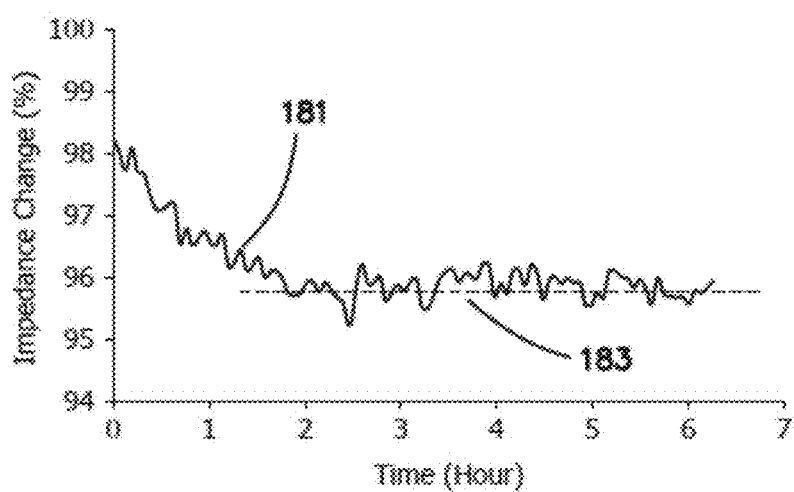

FIG. 11 is a graph of impedance change as function of time of VEGF 165 (70 pg/mL) at 1000 Hz in a clinical CSF.

Figure 12:
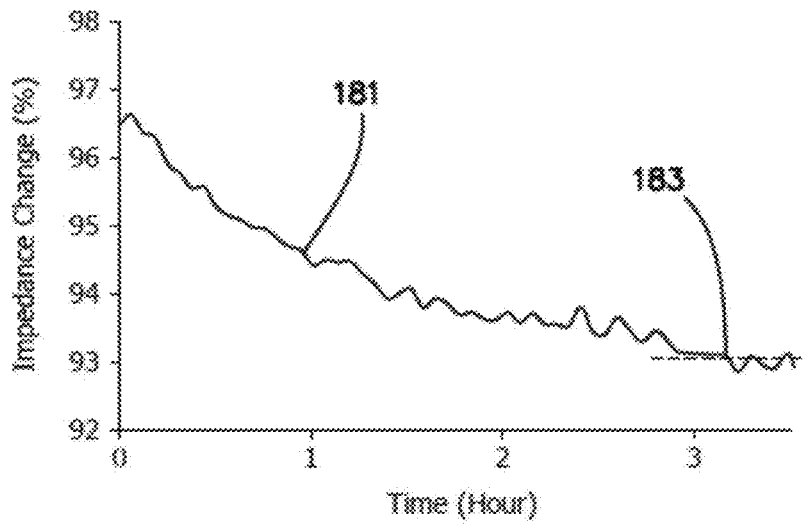

FIG. 12 is a graph of impedance change as a function of time of the VEGF 165 (200 pg/mL) at 1000 Hz in a clinical CSF.

Figure 13:
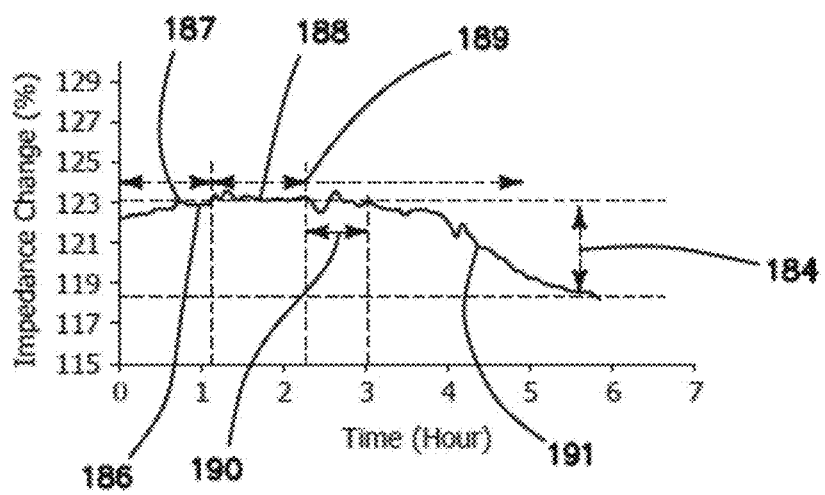

FIG. 13 is a graph of impedance change as a function of time of the PSA and VEGF 165 at 1000 Hz in a model solution.

Figure 14:
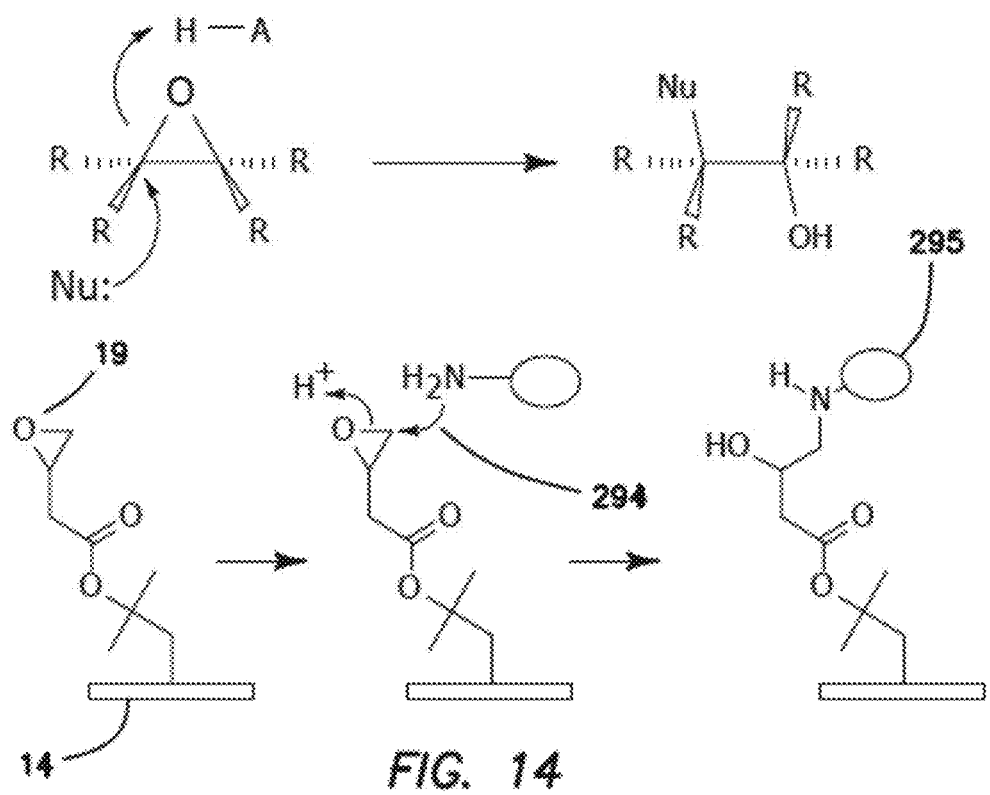

FIG. 14 is a molecular diagram of the functionalization of the carbon nanotubes using epoxide nucleophilic substitution chemistry.

Figure 15:
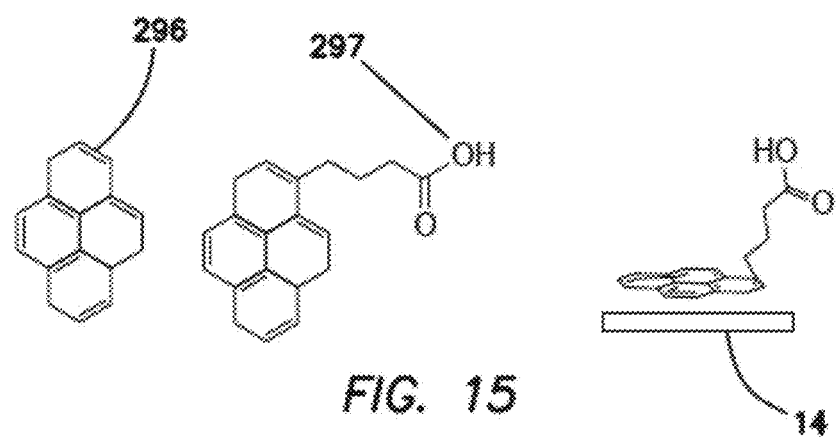

FIG. 15 is a molecular diagram of the process of functionalization of the carbon nanotubes using pyrene through π-π interactions.

Figure 16:
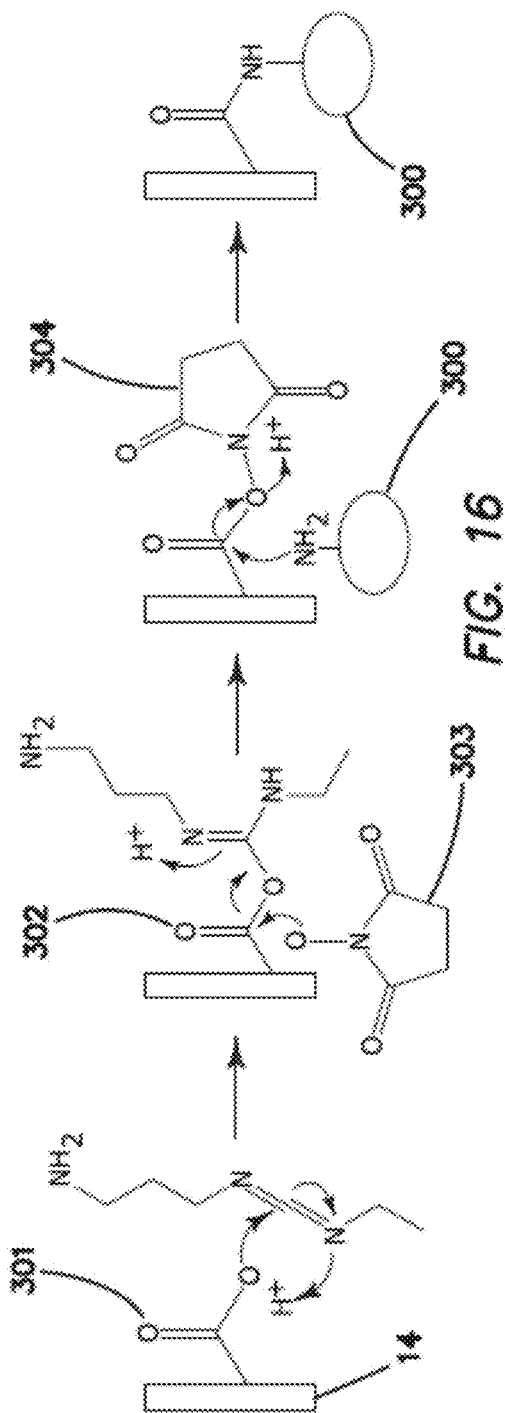

FIG. 16 is a molecular diagram of the covalent immobilization of antibodies to carboxyl groups through amide linkage.

Figures 17A, 17B:
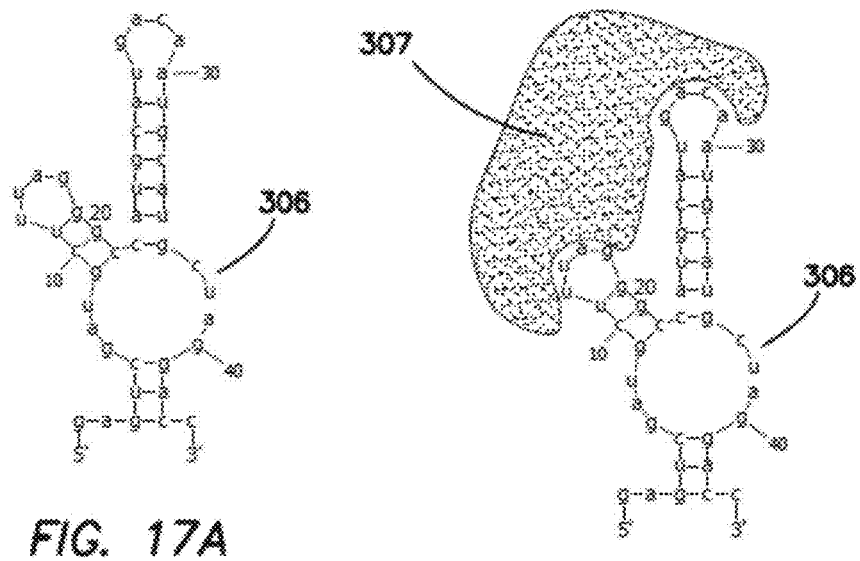

FIG. 17(a) is a molecular diagram of the interaction between the aptamer and single-strand oligonucleotides.

FIG. 17(b) is a molecular diagram of how aptamer binds antigen on the CNT's forming the substrate of the bioFET.

Figures 18A, 18B, 18C:
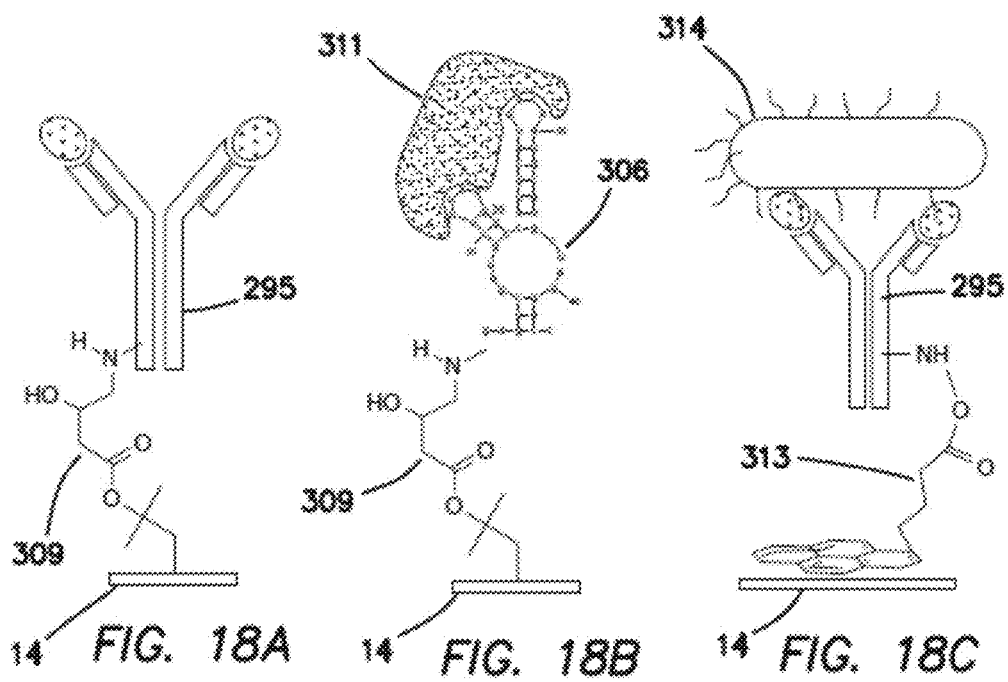

FIG. 18(a)-18(c) are molecular diagrams of the capture of analyte, proteins and microorganisms with the carbon nanotube bioFET sensor.

Figure 19:
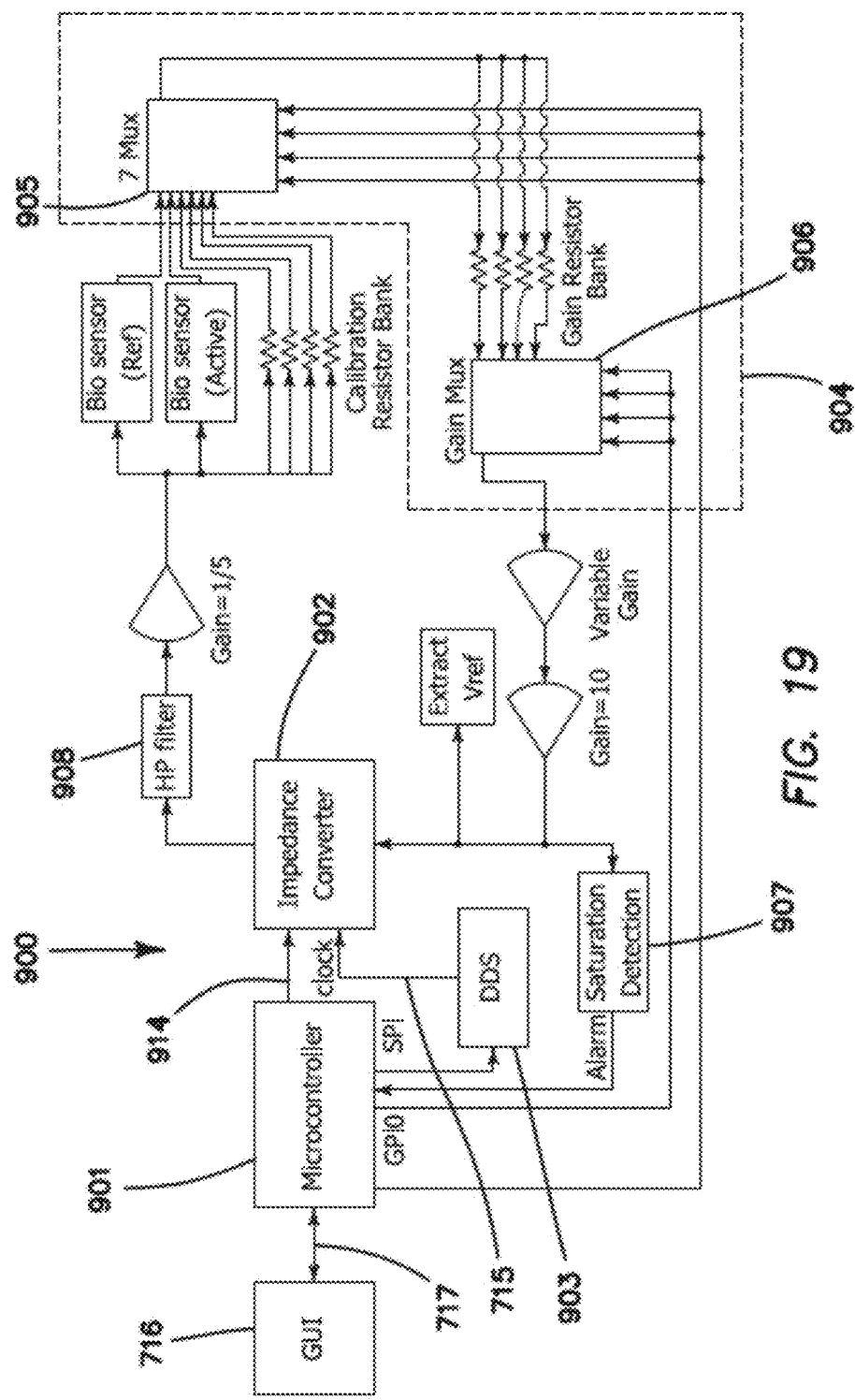

FIG. 19 is a block diagram of the electronic circuit, which detects specific biomarker antigen(s) in blood serum, CSF, and bacteria in food employing the bioFET sensor after appropriate surface modification on the basis of applications.

Figure 20:
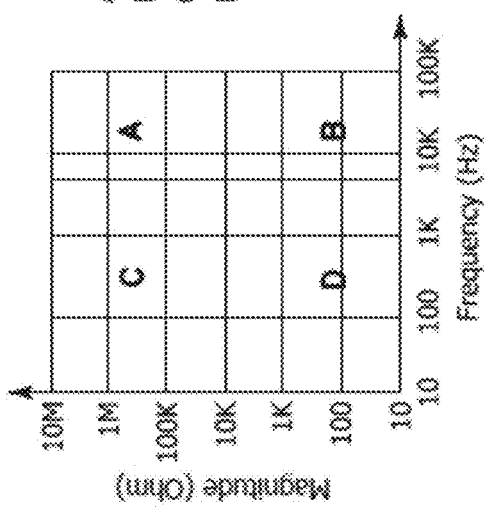

FIG. 20 is a graph representing the impedance coverage range, with and without employing the analog front end (AFE) and direct digital synthesizer (DDS).

Figure 21:
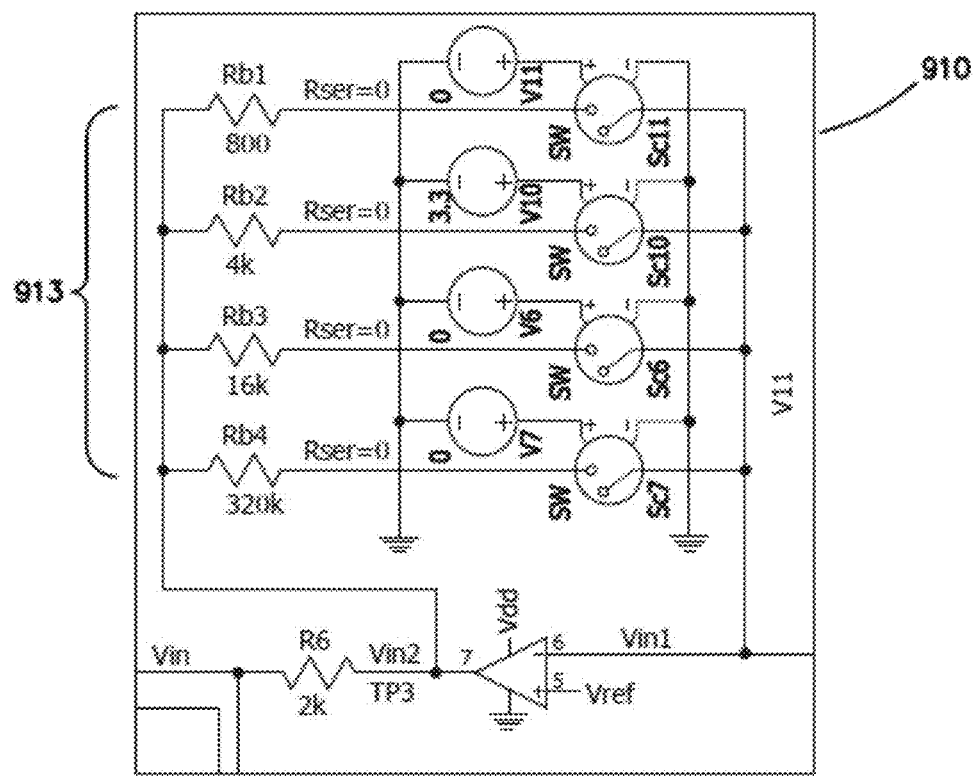

FIG. 21 is a schematic of a partial multi-gain stage post amplifier circuit that increases the range of impedance.

Figure 22:
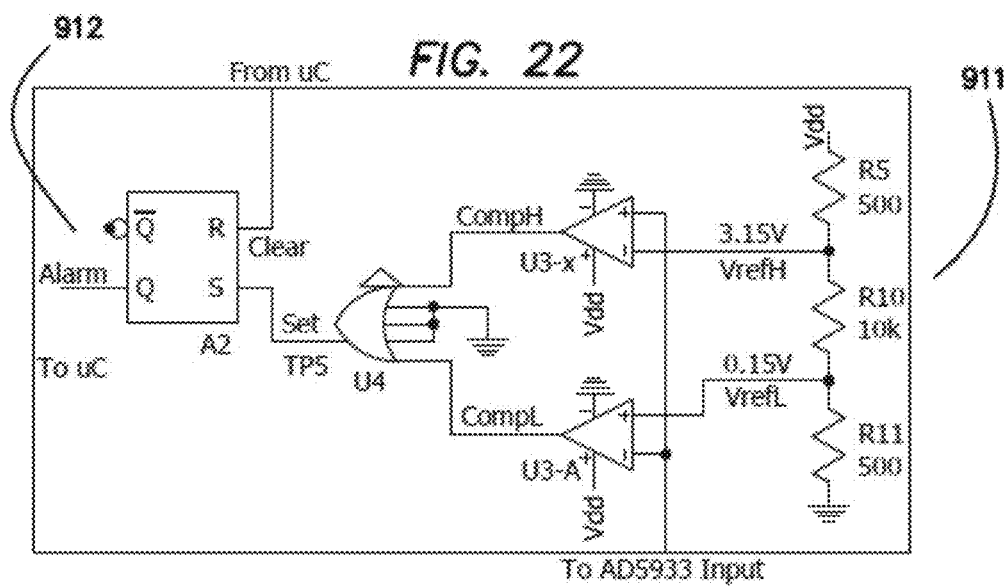

FIG. 22 is a schematic of a partial saturation detection circuit, which takes the post amplified signal (0 to 3.3 V) provided to the AD5933 impedance converter, and compares it with the high (VrefH=3.15 V) and low (VrefL=0.15 V) thresholds.

Figure 23:
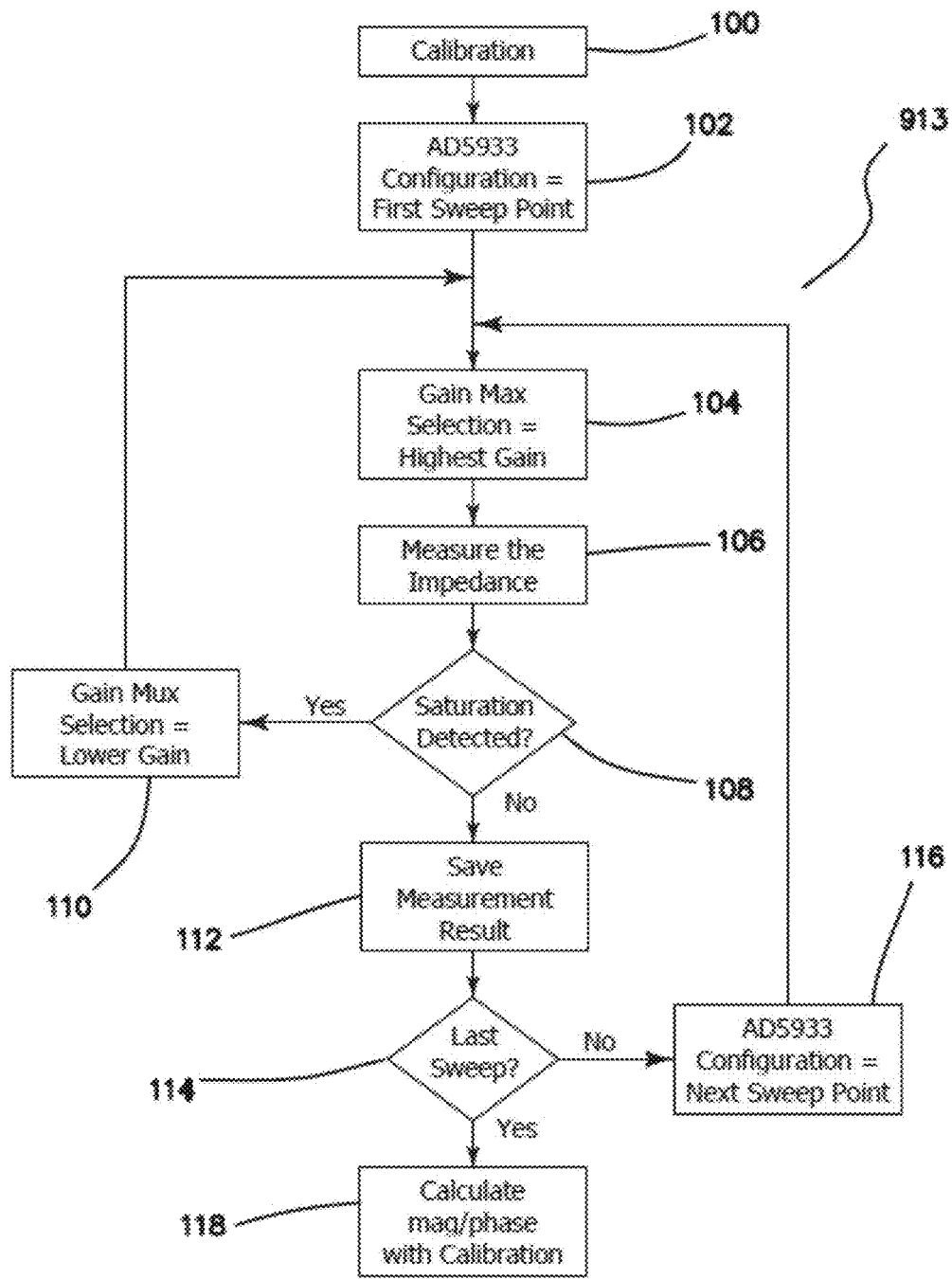

FIG. 23 is a flowchart detailing the auto gain selection software logic designed to select the proper post-amplifier gain based on the saturation detection circuit output to insure the impedance signal within the AD5933 impedance converter line.

Figure 24:
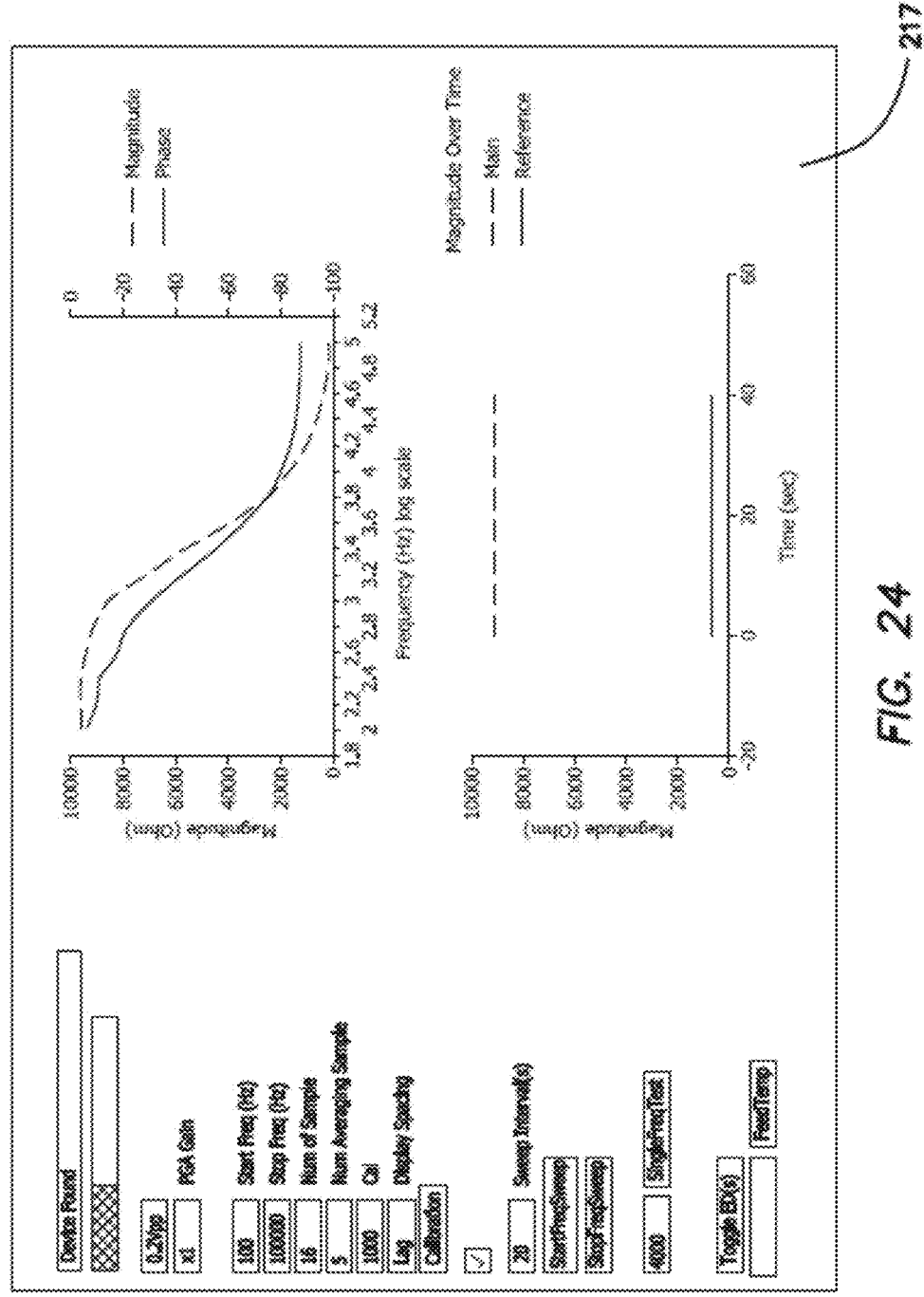

FIG. 24 is a screenshot of a graphic user interface (GUI) used in the apparatus of the illustrated embodiments.

Figure 25:
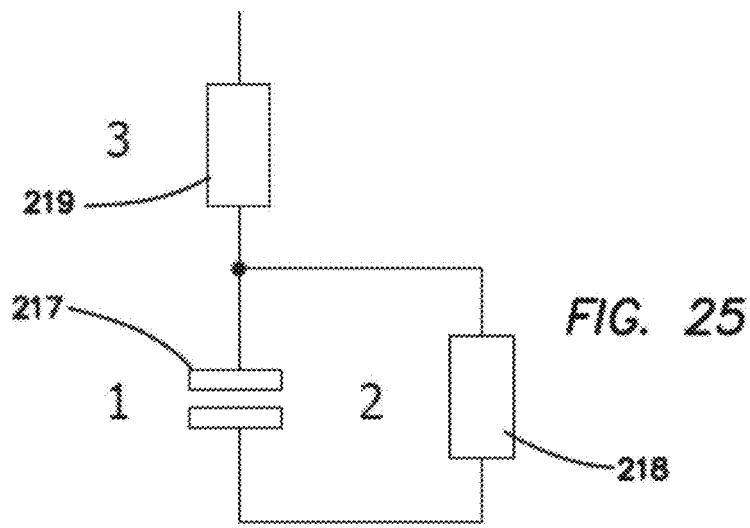

FIG. 25 is an equivalent circuit of the sensor and/or reference cell.

Figure 26:
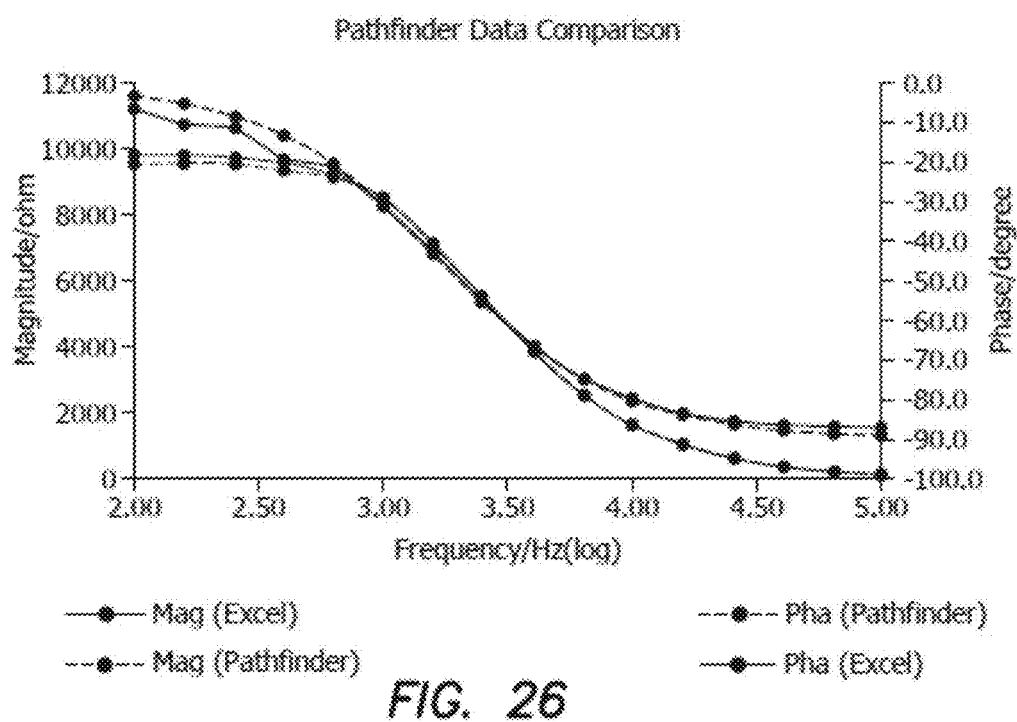

FIG. 26 is a graph of the impedance and corresponding phase change as a function of the applied frequency. The data were observed by pathfinder. Two sets of data were plotted together.

Figure 27:
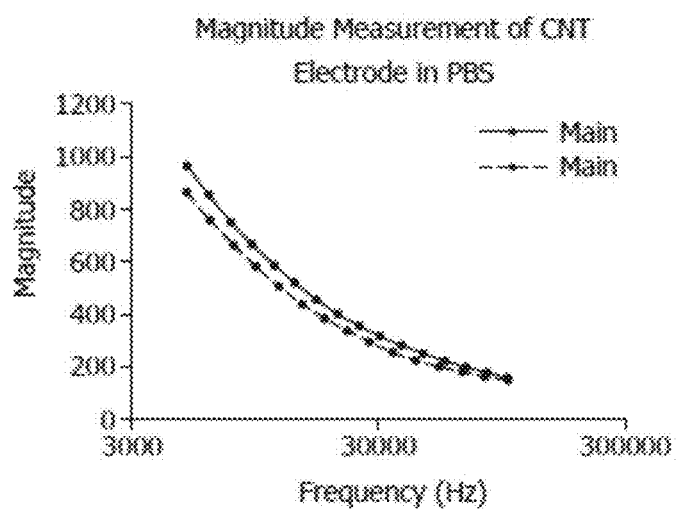

FIG. 27 is a comparison of the impedance between observed—Pathfinder and commercially available electrochemical impedance spectroscopy analyzer (Zahner, Model #IM6).

Figure 28:
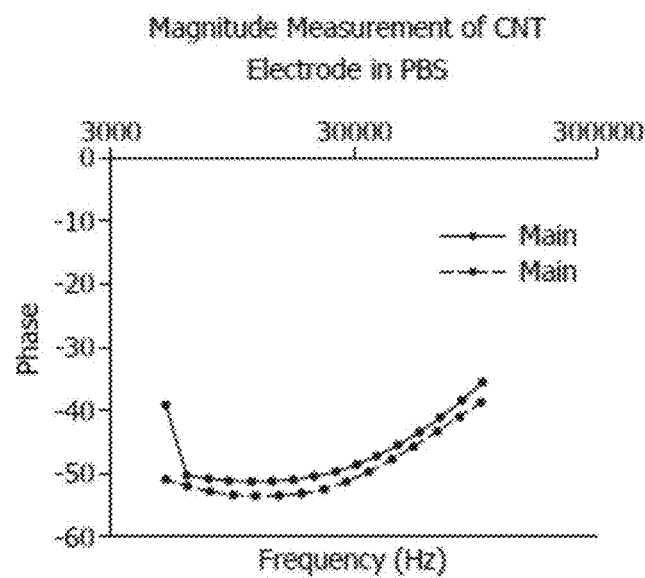

FIG. 28 is a graph comparing the phase of the detected signal observed by Pathfinder and a commercially available electrochemical impedance spectroscopy (Zahner, Model #IM6).

Figure 29:
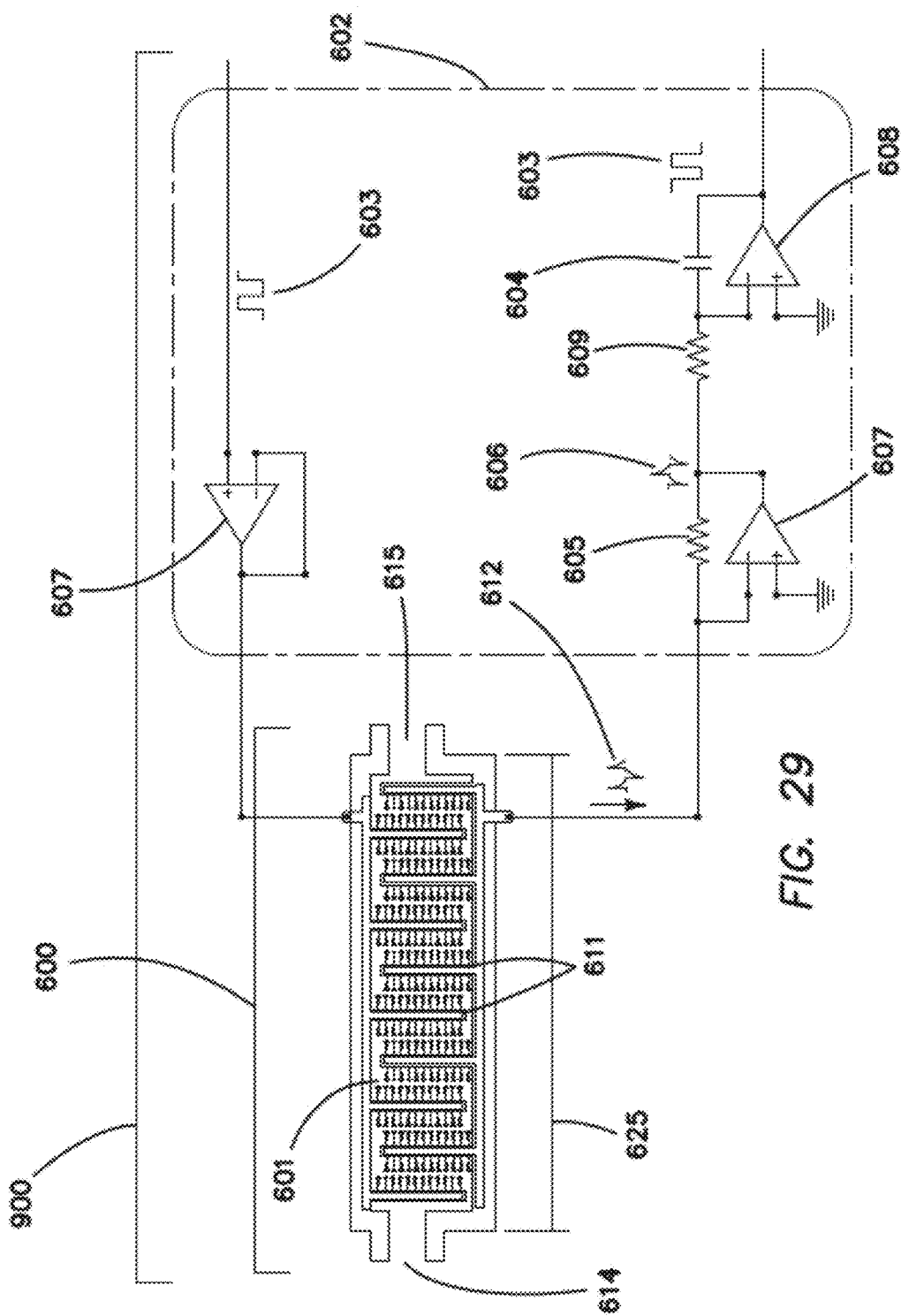

FIG. 29 is a schematic representation of the micro fluidic chamber with detail of the charging and discharging of the capacitive load on the bioFET cell's array.

FIG. 30A-30D are schematics for the computational circuits of the illustrated embodiment incorporating the principles of cellular bioFET array. FIG. 30(A) is the summing amplifier, FIG. 30(B) the difference amplifier, FIG. 30(C) the integrator, and FIG. 30(D) the differentiator.

Figure 31:
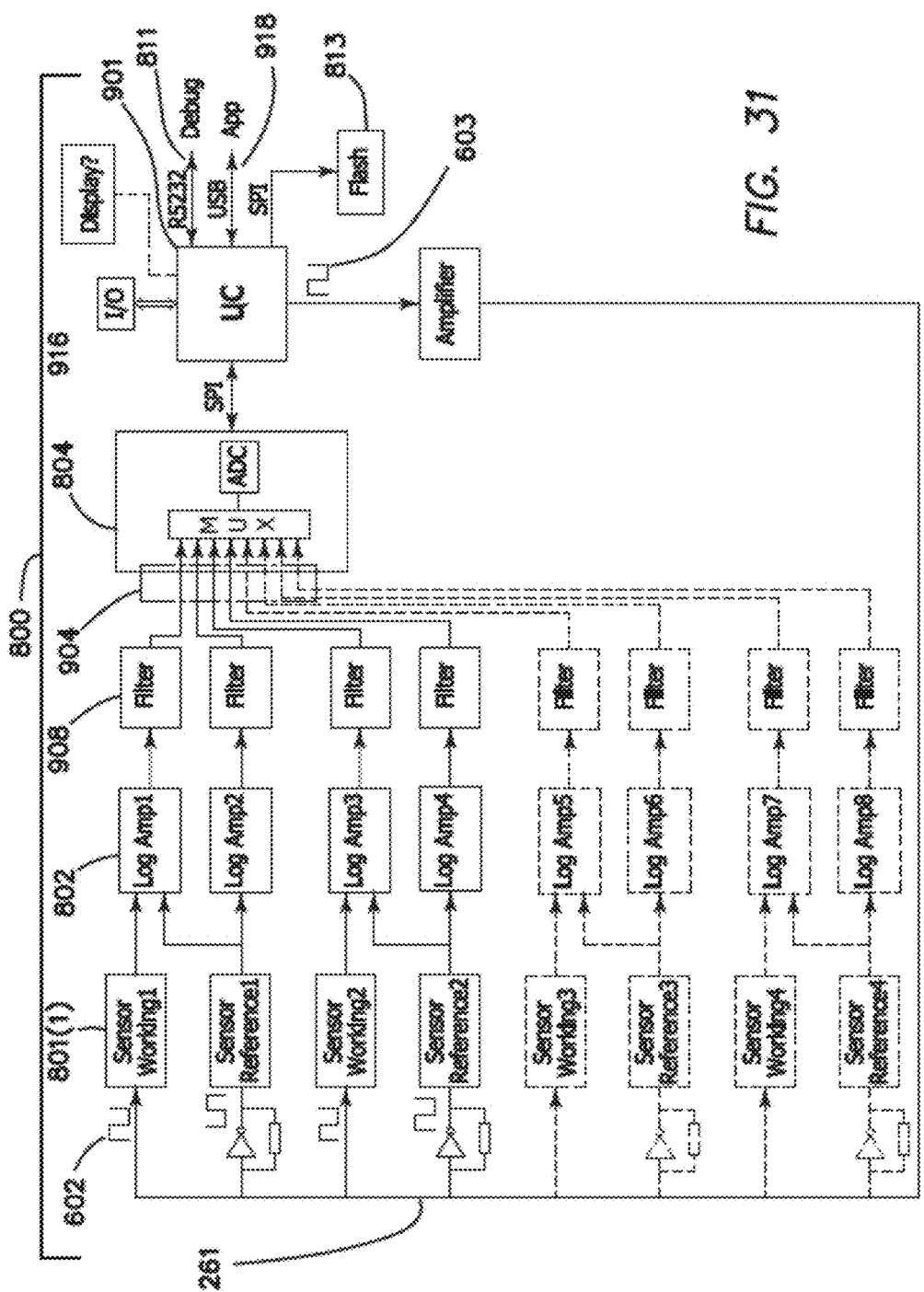

FIG. 31 is one example of a schematic representation of an analog front end (AFE) with selectively connectivity to the analog processing platform.

Figure 31A:
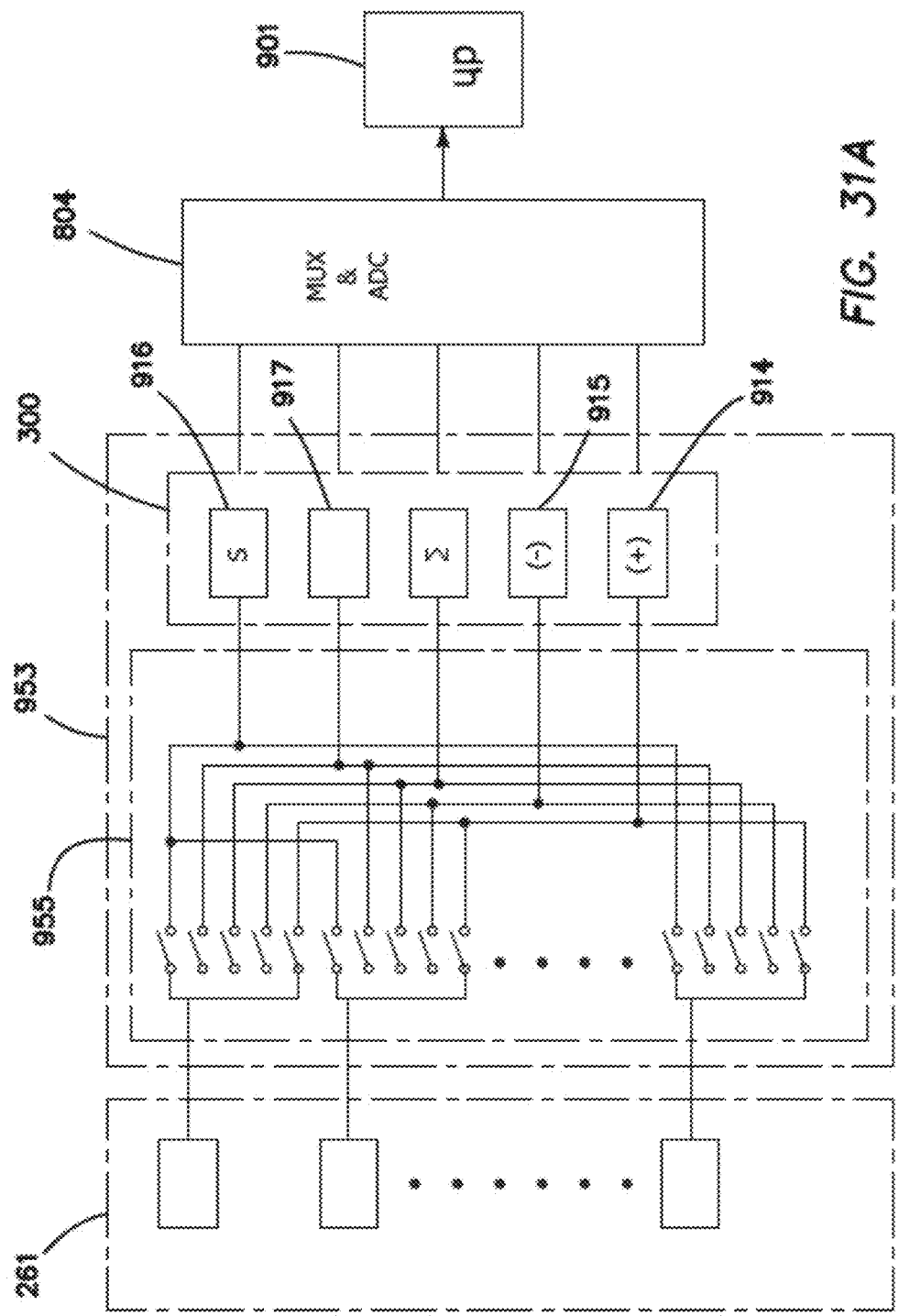

FIG. 31A is schematic representation of an addressable multiplexer (universal switch) module coupled to the output of an array of biosensors and thence to an analog arithmetic module before being multiplexed and digitized into a microcontroller.

Figure 31B:
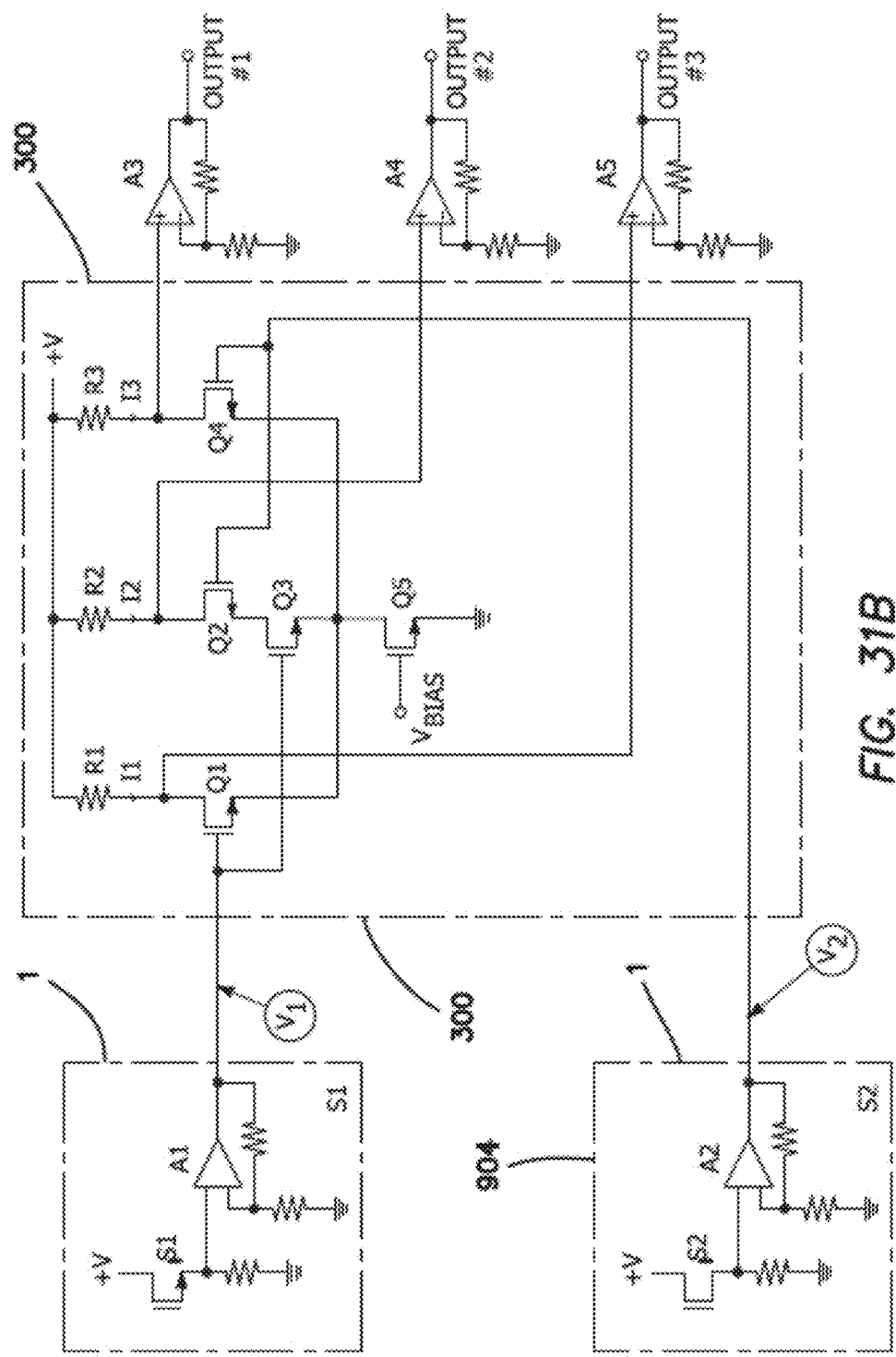

FIG. 31B is one example of a schematic diagram of the bioFET sensors $S_1$ and $S_2$ connected to the analog arithmetic module (AU), generating an operation on data generated by the bioFET sensor (tan h) and the derivative of the same function (d/dt of tan h).

DETAILED DESCRIPTION OF THE PREFERRED EMBODIMENTS

The BioFET Cell

Figure 1A:
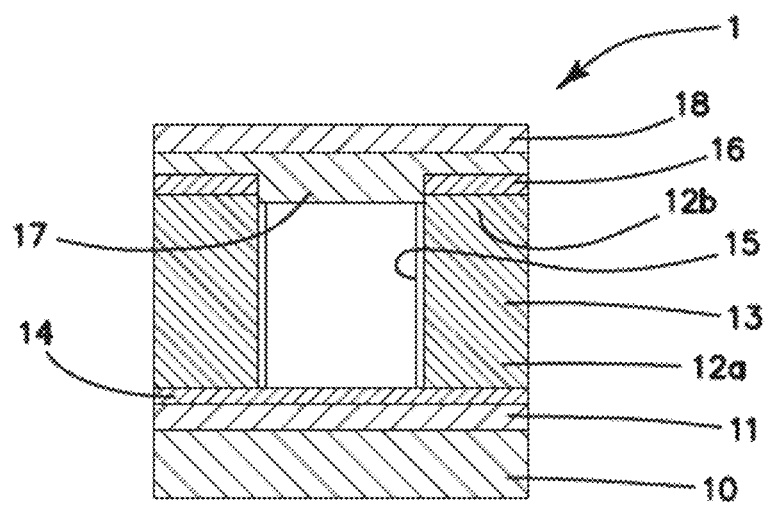
FIG. 1A is a side cross sectional view of a diagram of the bioFET sensor fabricated using conventional photolithography.

FIG. 1A is a diagrammatic cross sectional view of the bioFET cell 1 fabricated by conventional photolithography. A silicon (550 µm) wafer is used as a substrate 10. A nonconductive layer 11, such as $SiO_2$, is disposed on substrate 10 and used to isolate the Si substrate 10 from semiconducting carbon nanotube channel 14. The metal electrodes forming the opposing sides of the cell 1 are each fabricated of three layers, namely a chromium (Cr) layer 12a with the thickness of 30 nm in contact with CNT layer 14, a gold layer 13 with the thickness of 200 nm disposed on layer 12a and a chromium 12b with the thickness of 30 nm disposed on gold layer 13. The fabrication is finalized by covering the interior exposed surfaces of the metal electrodes with nonconductive $SiO_2$ layer 15 to avoid any electrochemical reaction between the metal electrodes and analyte that may occur during impedance measurement, since the electrodes serve only as electrical contacts and not data terminals. In the embodiment of FIG. 1A only the carbon nanotube layer 14 includes active material functionalized by antibodies. The gap between the two electrodes on opposing sides of cell 1 is approximately 2 mm and the final height of the electrode is 560 nm. The effective geometrical volume of a single sensor is 2 mm×2 mm×560 nm. The base of gate 18 is 2 mm thick and fabricated separately from a rigid nonconductive substrate. A metal layer 17 is disposed on the lower surface of the nonconductive substrate 18, which is covered by a 0.5 mm soft polymer layer 16 leaving a thicker exposed portion of metal layer 17 to form a counter electrode. The surface height of the exposed portion of metal layer 17 forming the counter electrode as measured from CNT layer 14 is slightly less than that for layer 16. The area of the exposed metal (counter electrode) 17 is less than the area of the bioFET, e.g., 1.8 mm×1.8 mm, so that the counter electrode (the gate 18) is properly placed on and between the side electrodes. The soft polymer layer 16 forms a sealed chamber within the bioFET cell 1. All the geometries of the device are scalable and tunable to parameters associated with the electrochemistry and dimensions of the molecule (analyte).

Figure 1B:
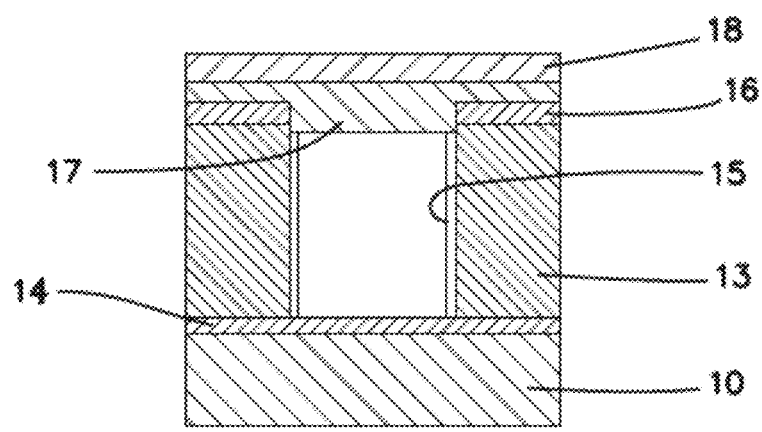
FIG. 1B is a side cross sectional view of a diagram of the bioFET sensor fabricated using conventional inkjet or screen printing methodologies.

FIG. 1B is a diagram of another embodiment of the bioFET cell or sensor 1 fabricated using inkjet and screen-printing methods. The advantages of this embodiment are: (1) reduction of the number of steps in fabrication of the metal electrodes, (2) reduction the height of the electrodes scalable to several micrometers, hence tunable, (3) mass production capability, and (4) more cost effectiveness. In this embodiment the layer 14 of carbon nanotubes is deposited directly on the surface of the substrate 10. A silver or gold layer 13 is printed without any pre-layers to form the electrodes. Finally, a nonconductive layer such as epoxy (SU-8) 15 is used to cover the interior surfaces of the metal electrodes so only the carbon nanotubes 14 will be exposed to the analyte. The critical geometry of the device is 2 mm×2 mm×7 µm. The counter electrode 17 is fabricated as before. All the geometries of the sensor can be changed if necessary.

Figure 2:
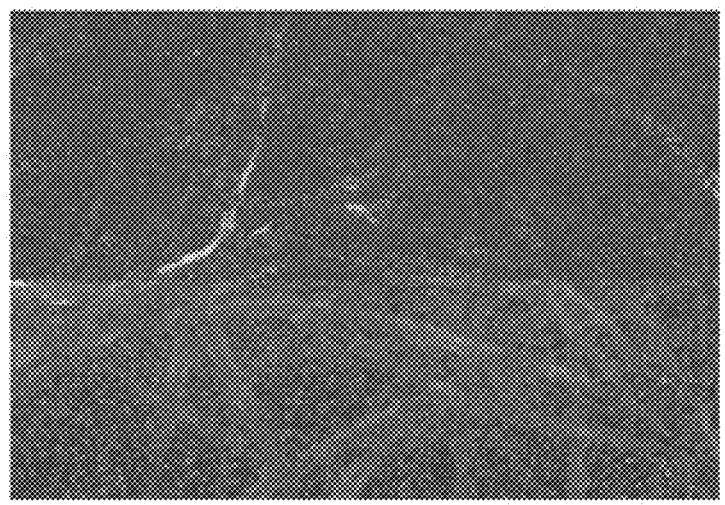
FIG. 2 is a scanning electron microscopic (SEM) image of dispersed s-SWCNT's (98%).

FIG. 2 is a typical scanning electron microscope image of dispersed semiconductive single wall carbon nanotubes, sSWCNT, with a purity of 98% semiconductive quality is used (2% metallic and 98% semiconductive in nature) and where its purity is governed by its chirality indices of n−m=3x. Nanotubes are members of the fullerene structural family. Their name is derived from their long, hollow structure with the walls formed by one-atom-thick sheets of carbon, called graphene. These sheets are rolled at specific and discrete ("chiral") angles, and the combination of the rolling angle and radius decides the nanotube properties; for example, whether the individual nanotube shell acts as a metal or semiconductor. Nanotubes are categorized as single-walled nanotubes (SWNTs) and multi-walled nanotubes (MWNTs). Individual nanotubes naturally align themselves into "ropes" held together by van der Waals forces, more specifically, pi-stacking. The way the graphene sheet is wrapped is represented by a pair of indices (n,m). The integer's n and m denote the number of unit vectors along two directions in the honeycomb crystal lattice of graphene. If m=0, the nanotubes are called zigzag nanotubes, and if n=m, the nanotubes are called armchair nanotubes. Otherwise, they are called chiral. Because of the symmetry and unique electronic structure of graphene, the structure or chirality of a nanotube strongly affects its electrical properties. For a given (n,m) nanotube, if n=m, the nanotube is metallic; if n−m is a multiple of 3, then the nanotube is semiconducting with a very small band gap, otherwise the nanotube is a moderate semiconductor. Thus all armchair (n=m) nanotubes are metallic, and nanotubes (6, 3), (9, 6), etc. are semiconducting. Further qualities of using s-SWCNT's and its electrical characteristics as used in this application when forming the bioFET cells 1 on $S_iO_2$ substrate. The process of forming the semiconductive layer (connecting between the source and the drain electrodes of the newly formed bioFET) the carbon nanotubes are dispersed in a solvent such as tetrahydrofuran (THF) and dimethylformamide (DMF) by a micro-probe sonicator for 15 minutes. The suspension of the s-SWCNT is stable for average of two years. These suspended sSWCNT are used to fabricate the active sensing element in cell 1 as shown in FIGS. 1A and 1B.

FIGS. 3A-3D are schematics of the concept of antibody attachment onto the surface of carbon nanotubes and capture of corresponding biomarker. FIG. 3A diagrammatically depicts the carbon nanotube layer 14. Polyglycidyl methacrylate (PGMA) 19, a polymer with epoxy functionality, is used to link between carbon nanotubes and the antibodies 20. The epoxide group of PGMA 19 binds directly on to the surface of the carbon nanotubes 14 as shown in FIG. 3B as well as with the amino ($NH_2$) functionality in antibodies 20 as shown in FIG. 3C. Using this polymer 19 as binding on to s-SWCNTs 14 and is used to enable an efficient electron transport by the carbon nanotube layer 14, response time and sensitivity of the sensor is improved. The immobilized antibodies 20 then capture only the target biomarkers 21 as symbolically shown in FIG. 3D.

Figure 4:
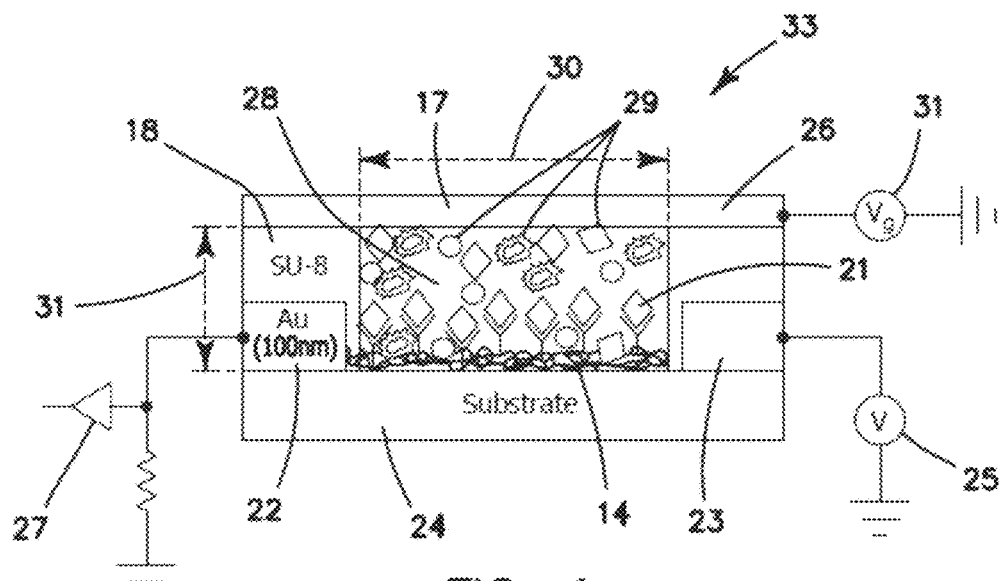
FIG. 4 is a side cross sectional view of a diagram of the bioFET sensor with its source follower amplifier, further describing the external electrical connections and analyte representation within the volume formed out of the source-drain and gate's geometry.

FIG. 4 is a cross-section of the bioFET cell 1 which includes: a nonconductive substrate ($SiO_2$) 24, and/or Kapton; a gold electrode 22 acting as the source for the bioFET coupled to a high input impedance source follower amplifier 27 (e.g. source follower amplifier (SFA) acting as a buffer amplifier to provide electrical impedance matching from the bioFET 33 circuit to the analog front end described (shown in FIG. 19). The SFA 27 is employed as basic single-stage field effect transistor (FET) amplifier, and in this application serves as a voltage buffer. In circuit 33 the gate terminal 26 of the transistor acts as the control input, the source 22 is the current output and the drain 23 is coupled to a selected voltage source, shared between the input and output. In addition, this circuit is used to transform impedances. (Thévenin resistance of a combination of a voltage follower 27 driven by a voltage source with high Thévenin resistance is reduced to only the output resistance of the voltage follower—a small resistance). That resistance reduction makes the combination of the bioFET cell 33 and source follower 27 a more ideal voltage source. Conversely, a voltage follower inserted between a driving stage and a high current load (i.e. a low resistance) presents an infinite resistance (low current load) to the driving stage—an advantage in coupling a voltage signal to a large load, as it is typical for biosensors in this application.)

An electrode 23 acting as the drain for the bioFET cell 1 carries the drain current. The counter electrode 17 forms part of the gate 18. The semiconductive single-walled carbon nanotubes (s-SWCNTs) 14 form the semiconductive channel between source 22 and drain 23. An electrolytic medium 28 contains various non-specific proteins 29 and the specific target biomarker 21 captured by the antibodies 20. A nonconductive layer such as $SiO_2$ insulates the electrodes 22, 23 from the counter electrode 17 and the surface of the s-SWCNTs 14, which extends the distance 30 between the source 22 and the drain 23. The incorporation of a high impedance source follower amplifier 27 increases the signal output, hence improving signal fidelity, reducing signal-to-noise ratio, and expanded dynamic range. The use of the source follower amplifier at the local site of or situated proximately to the bioFET cell 1 enables the simplification of the electronics by eliminating the use of an wikinverting amplifier and providing for a unity gain voltage buffering function, and where the voltage signal source has sufficient amplitude, but has a large internal resistance, and where the signal needs to be supplied to a "load" with much smaller resistance because the load on the s-SWCNT's hybridized a biological "payload" requires temperature control to avoid conformational changes of the protein in the payload.

To recap the bioFET cell 1 is a carbon nanotube based bio-impedance sensor using established field effect transistor (FET) technology. High purity, semi-conductive single walled carbon nanotubes (s-SWCNTs) 14 are used as a channel in the volumetric cell between the source and drain. The impedance of the target s-SWCNTs channel 14 is on the order of 100 kΩ. The randomly oriented carbon nanotube (CNT) based semiconducting channel 14 is modified and functionalized with antibodies 20 to capture target biomarkers 21, thus transforming the device from a classic FET into a bioFET. The CNT channel 14 is a monolayer of s-SWCNTs. Source 22 and drain 23 is fabricated using silver or gold ink jet printed-electrodes. The top gate 17, i.e., the controlled electrode, is fabricated using silver or gold ink jet printed layer on the surface of the top part of the flow cell 1. The dimension of the control electrode 17 is defined under a guideline set by the effective sensor geometry as a volume (2 mm×2 mm×7 μm) of an active area of a single device to achieve a high ratio capacitive load relative to a minimum surface area while employing a boundary condition of the flow characteristic of the channel defined between the source and drain electrodes. The separation gap between the counter electrode 17 and s-SWCNTs channel 14 is several hundred nanometers to a few millimeters in range, i.e., it is tunable. Distance 30 between the source and drain is 2 mm. The source and drain is covered by the nonconductive layer 26 such as epoxy (SU-8). The aqueous solution 28 containing the analyte 21 and the buffer act as a mediator and form the dielectric of the cell 1 prior to hybridization. It acts as the medium between the surface of s-SWCNTs layer 14 and the counter electrode 17.

Electrical and Flow Dynamic Factors of the BioFET Design

Multiple geometrical layouts are available to realize the bioFET cell architecture and to accommodate the two fundamental principles guiding the metrics of the cell 1, namely the flow characteristics of the buffer and analyte. Specifically, the molecular size of the item desired to be measured such as VEGF-165 molecule ranges between 35-50 kDa, while *E. coli* bacteria and larger proteins measure between 200,000 kDa to 500,000 kDa. The bioFET cell 1 is tested and evaluated in terms of transistor performance parameters. Families of I-$V_{ds}$ and I-$V_g$ curves reveal essential device characteristics (DC) related to the performance of bioFET cell 1 acting as a biosensor. These parameters include: transconductance, threshold voltage, on/off ratio, carrier mobility, etc. For the gate dependent study, a "liquid gate" configuration is used, where the gate voltage is actually applied through a metal path (i.e., control electrode 17) submerged in or in contact with an electrolyte solution 28. This liquid gate configuration has been demonstrated by many research groups to be an order of magnitude more effective in terms of electrical performance characteristics than conventional solid phase gating in Si/$SiO_2$ supported gated nanotube devices. For the gate electrode 17, we employ the common Ag/AgCl electrode used in the characterization of many nanotube FET devices, as a silver chloride electrode is a commonly employed reference electrode, e.g., like the internal reference electrode in pH meters. The electrode functions as a redox electrode and the reaction is between the silver metal (Ag) and its salt-silver chloride (AgCl, also called silver (I) chloride). Applying a DC voltage (e.g., 50 mV) and a superimposed AC potential (e.g., 5 mV) between source (S) 22 and drain (D) 23, electrical current flows from the source 22 to the drain 23 through the carbon nanotube network 14. The ratio of the AC voltage to the drain AC current, measured at a specific frequency (e.g., 100 Hz), provides the impedance value of the system output. The frequency is swept as described below to show a resonance. Time dependent studies will show a saturation level.

Figure 5:
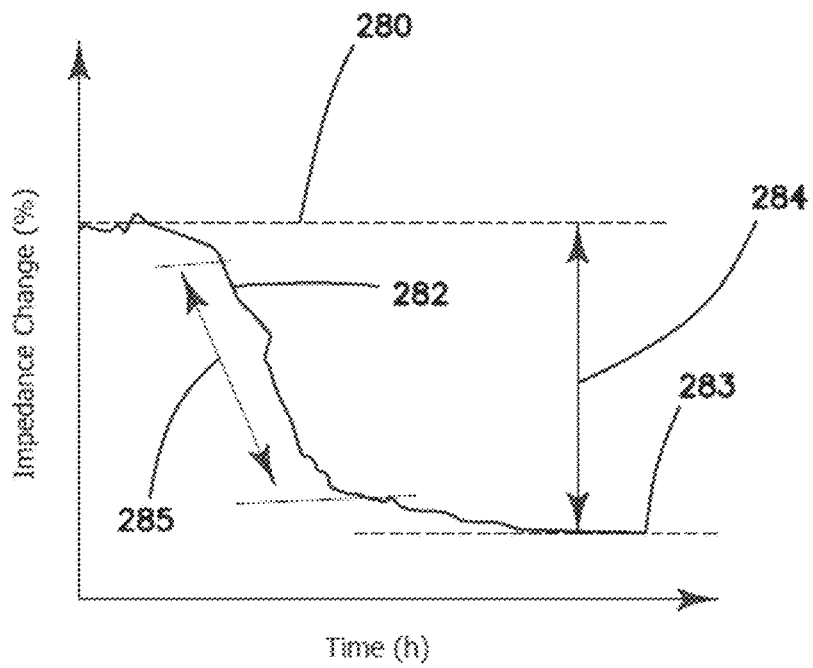
FIG. 5 is a graph of the signal obtained from the sensor of FIG. 4.

Biological receptors such as antibodies 20 (also called capture probes or ligands) specific to target biomarkers 20 are physically bound to the surface of the nanotubes 14 via a single step linking process. When target biomarkers 21 are captured by the antibodies 20, the binding event will cause a change in the impedance. The amount of signal 284 in FIG. 5 generated is inversely proportional to the concentration of biomarkers in the sample for a narrow range of concentrations, called the dynamic range 285 (FIG. 5). The curve represents the logarithmic output of the bioFET in operation. BioFET devices usually have a narrow response range. The typical "S" shape (reverse) of a response curve 282 is illustrated in FIG. 5, where the signal intensity is plotted as a function of the biomarker capturing time. At low analyte concentrations, still below the detection limit, the sensor 1 can only display baseline signal 280. Once the threshold concentration is reached (limit of detection, LOD) the sensor 1 will produce response signals linearly proportional to the concentration of the analyte which has bound (if plotted in logarithmic scale). This linear response typically spans one or two orders of magnitude of analyte concentrations. As the analyte concentration continues to increase, the sensor surface will be saturated, and the lower limit of response is reached 283. At the lower level, further increase in, for example, VEGF concentration as analyte, the plot indicates saturation and generates a constant response as the capacitive load reaches its maximum coverage threshold within the geometry of the bioFET effective area.

There are many factors that influence the dynamic range 285 of biosensors, including the binding affinity of antibodies, sensor geometry, number of active receptors on the surface, sensitivity of the transducer, etc. The bioFET sensor dynamic range is tuned to its specific application by optimizing the device geometry, as defined by the effective flow geometry as well as the distance between control electrode and the s-SWCNTs surface.

Arrays of BioFET Cells

FIGS. 6A and 6B are diagrams of two separate array designs considered in order to maximize the signal output of a plurality of bioFETs 1 by coupling or organizing bioFETs 1 in parallel, where in FIG. 6A the electrode pad 251 acts as the electrical connection to the array of single bioFET sensor cells 252, mounted on the non-conductive substrate 250 such as $SiO_2$ or any alternative polymer material. In an alternative configuration for the bioFET cell 1 in FIG. 6B we employ the embodiment of item bioFET sensor cell 253, whereby the surface area geometry is scalable in order to accommodate varieties of proteins with a weight several kDa to several hundred-thousand kDa such as *E. coli* bacteria with a weight between 200,000 kDa to 500,000 kDa.

Figure 7:
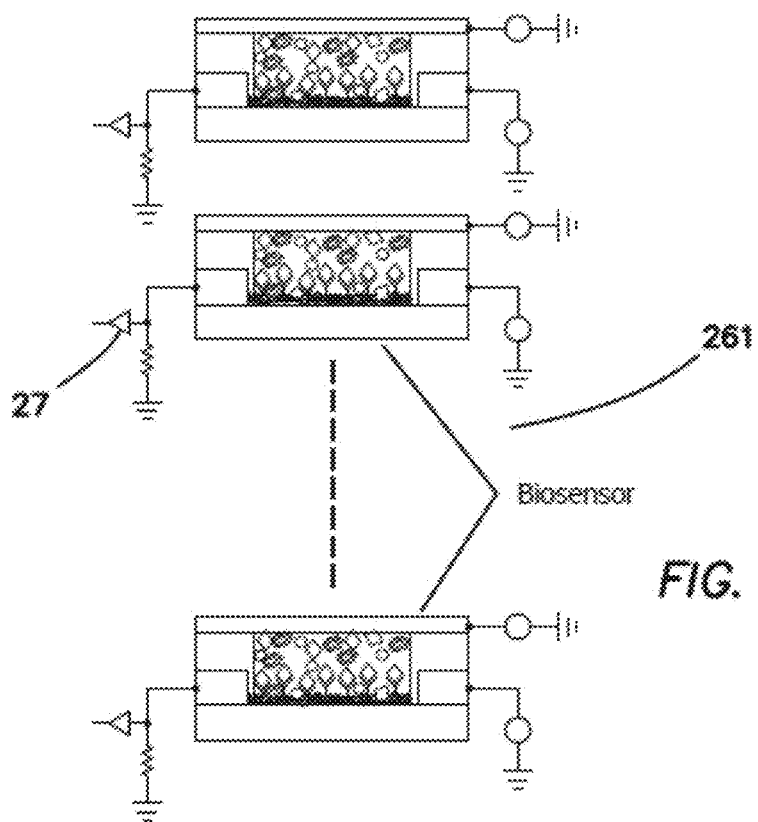
FIG. 7 is a diagrammatic schematic of the array configuration of bioFET cell units each with a source follower amplifier.

FIG. 7 is a schematic of a plurality of cells such as shown in FIG. 4 and their corresponding source follower amplifiers 27 are arranged into an array 261. The array configuration and its geometrical layout is a function of its use, the cells in an array can be arranged in an arbitrary number of dimensions and geometrical configurations, such as a square, triangle, hexagonal, or any other spatially arrangement. Topologically, the bioFET cells 1 can be arranged on an infinite plane or on a toroidal space, and the microfluidic chambers may assume a variety of hydodynamical topologies to improve fluid flow and obstruction avoidance due to sedimentation of proteins on chambers.

FIG. 7A is a geometrical representation an array of the bioFET cells 1 configured in a toroidal shape 600 and arranged in indexed and addressable cells of the microfluidic chamber $600.x_1, 600.x_2 \ldots 600.x_n$. The geometry proposed is similar to a doughnut but rather than having an empty central "hole", the topology of a torus folds in upon itself and all points along its surface converge together into a zero-dimensional point at the center called the Vertex. This makes it the perfect environment within which to populate the bioFET cell 1 and where the analyte flows through a toroidal manifold 600 which mimics the essence of an uninterrupted flow of the biological payloads of buffer and its constituents. Any input placed at the Vertex while the torus is "torsioned" (folded and rotated inward) is spread out and distributed over the entire surface of the toroid. This embodiment of flow characteristics provides for an improved use of the volumetric mass of the analyte; hence increases surface area exposure between the analyte and its antibodies, and increases the diffusion coefficient and hybridization rate.

FIG. 29 is a schematic representation of an array 600 of microfluidic chambers 1 and geometrical layout 600 of the bioFET array. There are many variations of geometry associated with such device and were the considerations which define the boundary conditions for such design are subject to the intended use and flow-rate considerations of the devices. Since the BioFET sensor array 261 and its apparatus 900 is intended for detection of antibody, an antigen, a protein, a receptor, an aptamer, a peptide, a DNA strand, or an enzyme, the metric designated as variable dimension (L) 625 of array 600 and flow characteristics may vary depending on the sampled assay employed by the use of the apparatus 900. The principle parameters are the type of fluid used, the dimensions of the fluid channels and the fluid's velocity in these channels. The relationship between these parameters can be expressed as the Reynolds number (Re), $$\left[ Re = \frac{\text{inertial forces}}{\text{viscous forces}} = \frac{\rho v L}{\mu} = \frac{vL}{v} \right],$$

which is a dimensionless quantity useful for determining the dominant profile in a flow system. Parameters such as density of fluid p, the mean fluid velocity V, the hydraulic diameter of the channel and fluid's viscosity p are general parameters for the microfluidic chambers. Typical parameter values for microfluidic chamber in an aqueous fluid are given to enable flow in a laminar fashion. FIG. 29 shows a network of micro-channels 611 included in the microfluidic chip (BioFET 1) connected to the outlet port 615 by input port 614 pierced through the chip. An optional geometry layout is shown in FIG. 7A where the number of cells 1 as well as their layout is subject to the intended use of the apparatus 900 in combination with the target analyte, such as the detection of an antibody, an antigen, a protein, a receptor, an aptamer, a peptide, a DNA strand, or an enzyme.

Charging and Discharging the Cell Array

In one of the embodiments, defined by FIG. 29 the details of the charging and discharging circuits 602 are shown. The circuit is set to measure the RC time constant, ($\tau$), where the time constant (in seconds) of an RC circuit, is equal to the product of the circuit resistance (in ohms) and the circuit capacitance (in farads), i.e. $\tau = R*C$, which is the time required to charge the capacitor (dimensionally shown in FIG. 1A of the bioFET 1), through the resistive load, by ≈63.2 percent of the difference between the initial value and final value or discharge the capacitor to ≈36.8 percent. This value is derived from the mathematical constant $(1-e^{-t/\tau})$ more specifically as voltage to charge the capacitor versus time, where the charging of the capacitive load is represented as $V(t)=V_0 (1-e^{-t/\tau})$, while the discharge obeys the function $V(t)=V_0 (1-e^{-t/\tau})$. The array is subject to a cycling of charging and discharging as discussed above. Circuit 602 has as its input a square wave 603 into an operational amplifier buffer 607, and includes a current to voltage amplifier 607, feedback resistor 605, an Op-amp integration circuit 608, with an input resistor 609, and a feedback capacitor 604. BioFET cell 1 has the equivalent circuit of FIG. 25, which includes a load resistance 219 coupled to a parallel capacitance 217 and resistance 218. The signal output 603 is the same as the input square wave 603. The half period of the input square wave 603 should be significantly larger than the RC constant formed by resistor 217, and capacitor 218 of bioFET 1, so that Op amp 607 has enough time to discharge the sharp transitions caused by the square wave 603. As the capacitance of bioFET sensor 1 increases with hybridization of target analytes 28, 20, the amplitude of the output signal 603, increases proportionally.

In one of the preferred embodiments, the microfluidic chamber 600 and its bioFET array is defined in a two-dimensional Euclidean space, like a grid (see cross section shown 600, or in the alternate geometry shown in FIG. 7A). In one example the chambers are organized as a parallel array in a defined geometry. But it is possible to arrange the cells into a three dimensional space. However, the cells in an array can be defined in an arbitrary number of dimensions and geometrical configurations, such as square, triangle, hexagonal, or any other spatially arrangement. Topologically, the bioFET cells 1 can be arranged on an infinite plane or on a toroidal space (see FIG. 7A) and the microfluidic chambers may assume varieties of hydodynamical topologies to improve fluid flow and obstruction-avoidance due to sedimentation of proteins on chambers walls. In other embodiments of this application the bioFET cell 1 is interconnected with series or parallel interconnections suitable for measuring hybridization of e.g. antibody, an antigen, a protein, a receptor, an aptamer, a peptide, a DNA strand, or an enzyme.

Sensor and Reference BioFET Cell Pairs

FIG. 8 is a diagram of the microfluidic chamber assembly divided into a bottom section 201 of the fluid flow cell and the top section 202. The top section 202 acts as the cover to the microfluidic channel incorporating the gate 209, i.e., counter electrode 17, the distance between the gate electrode 18 and the internal chamber active surface 14 is defined as the effective sensor geometry providing the unit measure of capacitive/impedance per unit of surface area of the gate 209. The microfluidic chamber is fabricated from a polymer employing a three dimensional printer. It can also be fabricated on glass, ceramics and metal using etching, deposition and bonding, polydimethylsiloxane (PDMS) processing, thick-film and stereolithography as well as fast replication methods via electroplating, injection molding and embossing. The microfluidic chamber contains the following features which enable the flow of analyte and buffer in an aqueous form through the surface fluid channel inlet 203 and the fluid channel outlet 204 which passes through the device active area 210 which is sealed by an O-ring 205. Within the sealed chamber is the active area 210 set in the bottom section 201 containing the bioFET sensor cell 206 and neutral reference bioFET sensor cell 207, which provides output signal through the electrode pad 211. Each sensor and reference cell 206 and 207 respectively, has the architecture shown in the schematic insert 212 or the cell 33 of FIG. 4. Sensor cell 206 and reference cell 207 are identical or substantially identical in all circuit, geometric, chemical and material parameters, except that sensor cell 206 has been functionalized with an active antibody layer and reference cell 207 has not. The output of the sensor and reference cells 206 and 207 respectively can be differenced in the circuitry of FIG. 9 to obtain an output indicative of only the specific bioeffect of the functionalized bioFET or sensor cell 206.

A plurality of cell pairs 206, 207 of the type shown in FIG. 8 in an array form similar to FIGS. 6A, 6B, 7 and in a circuit architecture schematically depicted in FIG. 9, are each combined with analog interface 802 and digital processing unit 804 of apparatus 800, also called the pathfinder reader. The source follower amplifier 27 of each cell 1 (also referenced as cells 206 or 207) is coupled to a corresponding log amplifier 802. The use of logarithmic analog computational method is employed by the proposed circuit to widen the dynamic range of input operation of the bioFET 1. Logarithmic transduction affords advantages such as constant-precision sensing at any intensity (Weber's law) and is a requirement in designing circuit 900 which operates with a sweep frequency of 50 Hz to 100 kHz, and where such use is explored in one of its embodiments where the sweep frequency is capable of going to lower than 50 Hz with impedance range of 50Ω to 10 MΩ (resistance value lower than 100Ω, and up to 10 MΩ are available as optional mode). If the concentration of a hybridization factor is fixed, and as the analyte conjugation increases in value, it is eventually binds all the available antibodies molecules and saturates the number of bound antibody/analyte complexes available. In addition, if the number of binding sites for a complex is limited (due to the finite cells of bioFET 1 and its array 261 with their effective binding sites), these sites will eventually all be bound by complexes or optionally with a gene expression that saturates. These two sources of saturation limit the dynamic range of hybridization and recording available in apparatus 800. FIG. 9 shows a circuit approach that simultaneously alleviates both these saturation problems to widen the dynamic range. The log amplifier 802 has an output voltage $V_{out}$ is K times the natural log of the input voltage $V_{in}$, expressed as, Vout=$K_{ln}$ Vin+$V_{ref}$, where $V_{ref}$ is the normalization constant in volts and K is the scale factor. A filter 803 is then coupled to the output of each log amplifier 802 for the purpose of noise filtration. A multiplexer 804 multiplexes the analog outputs of the plurality of filtered log amplifiers and digitizes the analog signals in an included analog-to-digital converter. The data is then coupled to a computer 806 with a plurality of conventional input/output peripherals for data processing and display.

Performance Characteristics of Cells

In other embodiments, the bioFET cell array and apparatus 800 measure the "effective sensor geometry" which in this application, is the ability of the apparatus and proposed method to measure the physical landscape of the local hybridization (the equivalent captured area by the hybridization of the antibody with its analyte) to map or capture such biological activity relative to the spatial and temporal terms, (differentiating such data relative to time domain), while recording capacitive values by mapping such changes relative to spatiotemporal data reduction collected by the apparatus arithmetic logic unit 904 in FIG. 31 where multiplexer 804 enables the biosensor 1 to be processed by a selection of the mathematical operation(s) shown by example FIGS. 30A-30D. These electrical impedance values with their respective time stamps of saturation events enable tracking of biological sequences occurring on the bioFET 1.

The change in capacitive loading on the bioFET 1 and its impedance is directly related to its effective geometry, which is a term of art, identifying the surface or volume of the bioFET 1 available to capture analyte in a process of hybridization and its equivalent electrical change. These and other embodiments of the invention relate to scaling of the geometry of the bioFET array, relative to flow characteristics as well as obstruction of protein by sedimentation in the microfluidic chamber. The effective cross sectional area of the flow through the bioFET cell 1 must be larger than the cross sectional area of the flow inlet and outlet so that the physical geometry of the sensor does not impede the flow characteristics of the entire system. The capacitance due to the sensor geometry is described in Equation (i) using the dielectric ($\in_r$) as a variable which correlates with target analyte 29 concentration in the test sample.

$$C_{geometry} = \varepsilon_r \varepsilon_0 \frac{A}{D} \qquad (i)$$

Where A is the area of the source and drain electrodes functioning as a capacitive late, D is the distance between the source and drain electrodes functioning as capacitive plates, and $\in_r$ is the combined relative permittivity (dielectric constant) of the medium measured by the apparatus 800, consisting of e.g. a hybridized vascular endothelial growth factor (VEGF) molecules, a pH buffer, specific antibody to capture a VEGF molecule, (such as Pegaptanib sodium, Macugen; mfg. by Eyetech/Pfizer) Amino hybridization substance, $SiO_2$ insulator, and p-Si substrate; $\in_0$ is the permittivity of the free space ($\in_0$=8.8541878176×10$^{-12}$ F/m); A is the total area of electrode plates located between the source 22 and drain 23 electrodes (shown in FIG. 4) with width, and length shown for example on FIGS. 1A and 1B, and where D is effective geometry term, indicating the open space available for the biological conjugation of antibody, an antigen, a protein, a receptor, an aptamer, a peptide, a DNA strand, or an enzyme to occur between the electrodes 22 and 23. The values of A and D are chosen so that the electrical change in capacitance/impedance, due to hybridization, is effectively measured with the limitations associated with the circulation flow of the analyte through the bioFET sensor unit.

An exemplary expansion of the geometry of the bioFET array 261 is realized by reducing the geometrical terms to its metrics. Considering the fact that the thickness of the surface of VEGF165 bound to its antibody is approx. 200 nm, the separation between source 22 and drain 23 can be as small as a few micrometers without the risk of restricting the flow due to VEGF molecule-hybridization and sedimentation of residual nonspecific proteins. However, because the cross sectional area formed by $d_{cap}$, and $W_{cap}$, it must account for the molecular dimension in molecular weight value. Hence, the effective geometry cross sectional area of the corresponding flow inlet 614 and outlet 615 in FIG. 29 must follow the Reynolds (Re) fluid flow characteristics through the bioFET-chamber during the measured event, otherwise sedimentations bound to cause flow's obstruction.

Using an example for possible layout of the bioFET sensor array 261 within a microfluidic chamber 600, and given the dimension of 3 French (0.039 of an inch) inlet diameters 614, the aggregate minimum cross sectional area of fluid flow through the entire parallel array 261 of biosensors 1 is approximately 100 mm×8000 mm. The only free variable in Equation (i) is the combined dielectric constant ∈$_r$ that is the changes with VEGF molecule hybridization and the surface antibody chemical chain. In order to maximize the effective sensing area in a small volume, the bioFET 1 spacing between the gate and its source-drain 22, and 23 electrodes (see FIG. 1A) and arranged in e.g. interdigitated fingers pattern, to yield the desired results.

Using the example described above, the combined thickness of one bioFET cell-plate is 102.02 μm (the sum of the thicknesses of electrode, two layers of p-substrate, and two layers of insulator). With d (the distance between the source 22, and drain 23, and the gate height 17) is 100 μm, so it follows the total space required for each electrode pair is 202.02 μm. Because the plate area of 1 cm$^2$ provides sufficient capacitance of around 10 μF, A is chosen as 1 cm$^2$ and W$_{cap}$ (the width of the plates which is the distance between source 22 and drain 23 on one side and the gate 17 (structured as top of the bioFET cover), shown in FIGS. 1A and 1B, chosen as 0.8 cm, this exemplary geometry results in a total length of plates of 12500 μm. With Leap (the length of the plates) chosen as 625 μm, and where there are 20 bioFET cell pairs arranged in interdigitated finger pattern, Thus, the total internal volume of the array module is 8000 μm (D)×725 μm (H)×4040.4 μm (L). With the dimensions noted above the applicant, performed a study to confirm the process and validate the working assumptions used by the proposed application.

The measurement technique employed in computing the total output of the electrochemical cell, as noted by FIGS. 1A and 1B, is simply the bioFET 1 change of dielectric value associated the hybridization of the analyte/antibody and where ∈$_r$ is the combined relative permittivity and dielectric of the medium relative to the sweep frequency (∈$_r$(W) attenuating the capacitive load/impedance while changing the device characteristics (DC) of bioFET output (V$_{ds}$-I$_{ds}$).

In one embodiment, the invention teaches of an analog front end circuit 904 (shown in FIG. 9) which enables charging and discharging of the "effective space" between the source 22 and the drain 23 electrodes, to enhance polarity's kinetics between the analyte the electrochemical bioFET cell, at the appropriate frequency, and measure its equivalent capacitance from the average current in half-period, as is noted in Equation (ii), $$I_{avg} = \frac{\Delta Q}{T/2} = \frac{C\Delta V}{T/2} = 2C\Delta Vf \quad \text{(ii)}$$

Where ΔV and f, are known and I$_{avg}$ can be measured. This measurement technique is illustrated in circuit 602 in FIG. 29, which consists of two separate circuits. The op amp source follower 27 which increases the input impedance of the electrochemical bioFET cell 1 so that the cell can be driven by a near perfect square wave by a digital output signal line from a microcontroller 901. The frequency (f) of the square wave 603 is chosen as the maximum frequency that completely charges and discharges the capacitor in the electrochemical bioFET cell in the half period. The charging of the capacitor creates a charge field which allows the binding of the desired molecule and the discharging of the capacitor to free the molecules which bind due to ionic or electrical polarity. This allows the device 1 to bind and unbind nonspecific ionic molecules so that there is not a permanent build up or binding of nonspecific proteins due to ionic members within the buffer solution 28. The second part of square wave 603, converts I$_{avg}$, into voltage value with a known resistor value of resistor 605 and amplified with a pre Op-Amp 607. V$_1$ at the output of the Op Amp 607 is calculated as shown in Equation (iii).

$$V_1 = C_{cell} R_1 \frac{DV_{in}}{dt} \quad \text{(iii)}$$

An op amp integration circuit as a source follower arrangement converts the transient voltage values 606, into a square wave 603, as shown in Equation (iv).

$$V_{out} = -\frac{1}{C_2} \int \frac{V_1}{R_2} dt \quad \text{(iv)}$$

Substituting Equation (ii) into (iii), the output of circuit 602, as a function of its input can be calculated as shown in Equation (v) leading to Equation (vi).

$$V_{out} = -\frac{1}{C_2 R_2} \int C_{cell} R_1 \frac{dV_{in}}{dt} dt \quad \text{(v)}$$

$$V_{out} = \frac{C_{cell} R_1}{C_2 R_2} V_{in} \quad \text{(vi)}$$

The output voltage of circuit 602 sampled by an ADC 804, (shown in FIG. 9) is proportional to the value of C$_{cell}$. The multiplication of this principle as it is applied to an matrix of bioFET cells 261 in an array format and its selected optimal geometry terms, is provided to achieve the desired results of parallel detection and computing apparatus 904 suitable for the specificity of the measurement, or for mimicking of such dynamics, using multiple parallel geometrical arrangements as contemplated by the invention and its embodiments.

Proof of Concept Performance

FIG. 10 is a graph depicting the noise-filtered impedance measurement of apparatus 800 at 1 kHz with a model phosphate buffer solution (PBS) with a concentration of VEGF 165 of 5000$_{pg/ml}$. The curve represents the difference between reference sensor 207 and bioFET sensor 206 of FIG. 8 as percentage of the impedance change over time. The curve 182 further represents the change in capacitive loading due to hybridization of VEGF with its specific antibody. The introduction of the impedance change due to the binding of antibody 20 to the VEGF 165 target molecule 21 culminating in the saturation 183 of the signal 184 which indicates that the hybridization process is complete. This graph further demonstrates the effective use of the bioFET 1 as realized by the invention, the impedance value follows the "S" shape of the inverse relation in the time domain relative to hybridization (capacitive loading) and impedance value.

FIGS. 11 and 12 are graphs depicting the percentage difference between reference sensor 207 and bioFET sensor 206 of FIG. 8 of the impedance change at 1000 Hz as measured using clinical cerebro-spinal fluid (CSF) indicating the VEGF165 hybridization through a specific antigen 21 while immersed in a complex assay of multiple proteins. A clinical sample was used directly for measurement and the concentration of VEGF165 with concentration values of 70$_{pg/mL}$ and 200$_{pg/mL}$ respectively. These values where first established by ELISA method. The samples were supplied by the University of Southern California (USC) under contract. As indicated by the graphs a s signal change is observed immediately after insertion of the CSF, while hybridization of the VEGF165 molecule at a 70 pg/mL concentration occurs in the time domain after about 2 hrs in FIG. 11 indicating the statistical probability of the reflected solution ($70_{pg/mL}$) relative to the increase of hybridization in about 3 hrs due to increased concentration (of 200 pg/mL) in FIG. 12.

FIG. 13 is a graph representing the signal output associated with the percentage change or comparative capacitive/impedance change between reference sensor 207 and bioFET sensor 206 of FIG. 8 while measuring the output with the insertion of a buffer 187 (PBS) followed by the introduction of the control factor, such as prostate-specific antigen (PSA) (200 pg/mL) which shows that the impedance change was not observed within one hour of the test 186, and where the specific antibody for the $VEGF_{165}$ reacted to the insertion of the VEGF165 (200 pg/mL) by hybridizing and changing the capacitive load/impedance due to specific binding of antigen/analyte 189. This test confirms the efficacy of the biosensor functionalization relative to specificity of the binding agent.

FIG. 14 is a molecular diagram of the functionalization of carbon nanotubes 14 using epoxide nucleophilic substitution chemistry. The description provided below is an example of the chemical bonding of the carbon nanotubes 14 and its functionalized group while forming the bioFET effective geometry, resulting in the attenuation of the bioFET to generate the desired signal while hybridizing the analyte with its specific antigen. An antibody 295 or amino-modified aptamer can be covalently linked to the poly (glycidyl methacrylate) (PGMA) 19 coated carbon nanotubes 14 through a nucleophilic substitution reaction. The nucleophiles on the antibody (e.g. lysine residues and the amine-terminus) will attack the electrophilic carbon of the c-o bond, forcing the ring opening of the highly strained epoxide group 294. The nucleophilic ring-opening of the epoxide by amines results in the formation of a β-amino alcohol group on the PGMA polymer, with the antibody or amino-aptamer covalently attached to the PGMA 295. This nucleophilic substitution reaction between the epoxide groups on the PGMA and nucleophiles on the antibody allows for any antibodies and amino-modified aptamers to be covalently linked to the carbon nanotubes 14.

Molecular Modeling of Binding

FIG. 15 is molecular diagram of an alternate process of functionalization of the carbon nanotubes 14 using pyrene through π-π interactions. Non-covalent functionalization of the carbon nanotubes 14 can be achieved using pyrene 296 and pyrene derivatives 297. The aromatic groups on the pyrene and pyrene derivatives are bound to the surface of the carbon nanotubes 14 through non-covalent π-π interactions. The strong π-π interactions between the aromatic pyrene is a combination of electrostatic and van der Waals interactions. The geometry of interactions is determined by the electrostatic effects, while the van der Waals interactions contribute to the magnitude of the π-π interactions.

FIG. 16 is a molecular diagram of the covalent immobilization of antibodies 300 to carboxyl groups through amide linkage. Surface carboxyls on the carbon nanotubes 14 or the carboxyls on the pyrene 301, is activated using 1-ethyl-3-(3-dimethylaminopropyl) carbodiimide (EDC) 302 for direct conjugation with primary amines via amide bond linkage. The EDC-activated carboxylic acid forms an active O-acylisourea ester intermediate that can be displaced through nucleophilic substitution from the amines. To prevent rapid hydrolysis of the O-acylisourea ester intermediate, N-hydroxysuccinimide (NHS) 304 is added to the reaction, forming an amine-reactive NHS-ester that has improved the stability. The antibody 300 will be linked to the carboxyls through covalent amide linkage by displacing the NHS. This EDC/NHS immobilization process allow for any antibody or protein to be immobilized on the carbon nanotubes 14 through the covalent amide linkage between the amines on the antibody and carboxylic acid groups on the pyrene or on the carbon nanotubes themselves.

FIGS. 17A and 17B are molecular diagrams of the interaction between the aptamer 306 and single-strand oligonucleotides. FIG. 17A shows the interaction between the aptamer 306 and single-strand oligonucleotides and FIG. 17B shows a schematic of how aptamer 306 binds antigen 307. Aptamers are single stranded oligonucleotides (DNA or RNA) selected against a target molecule using systemic evolution of ligands by exponential enrichment (SELEX). Aptamers provide several advantages over antibodies including improved stability and site-specific modification of the aptamers to allow conjugation of a reporter molecule (dye) or a functional linker for immobilization, long self-life, and storage temperature, i.e., can be stored at room temperature for several months. The unique sequences of the oligonucleotides allow each aptamer to fold and adopt specific secondary and tertiary structure. The affinity and avidity an aptamer has for its target depends on how well the aptamer will fit into a cavity of the protein or target molecule. In other words, the binding between an aptamer and a target molecule is dependent on the surface residues of the antigen 307 and the structure of the aptamer 306.

FIGS. 18A-C are molecular diagrams of the capture of analyte with the carbon nanotube bioFET sensor. The carbon nanotubes 14 functionalized with PGMA can be used to covalently attach antibody 295 or amino-modified aptamer 306; while pyrene derivatives 313 can be directly tethered to the pristine carbon nanotube surface through π-π interactions. The carbon nanotube bioFET sensor functionalized with the aforementioned modification process can then be used to capture any target analyte 21 of interest ranging from small molecules such as glucose, nucleic acids in FIG. 18A, peptides/proteins 311 in FIG. 18B and microorganism including bacteria and viruses 314 in FIG. 18C.

Instrumentation Circuits for Analytic Processing in Cell Arrays

FIG. 19 is a block diagram of the electronic circuit 900, which detects specific biomarker antigen(s) 21 in blood serum, CSF, and bacteria in food employing the bioFET sensor 1 after appropriate surface modification on the basis of application on hand. In the embodiment of FIG. 19 time dependent measurement of the saturation of the sensor cell 206 is used as the data point. Circuit 900 includes a microcontroller 901, impedance converter 902, a direct digital synthesizer (DDS) 903, an analog front end (AFE) 904, a Z multiplexer (MUX) 905, a gain multiplexer (MUX) 906, and a saturation detection circuit 907. The circuit 900 operates with a sweep frequency of 50 Hz to 100 kHz. In one embodiment the sweep frequency is capable of going to lower than 50 Hz with impedance range of 50Ω to 10 MΩ, providing for example 16 sweep points to define the linear response curve. It is within the spirit and scope of the invention to increase the number of sweep points to augment the number of data points and to further improve the statistics so as to represent a smoother linear curve. The apparatus 900 also includes additional mathematical signal processing tools within the microprocessor e.g. using a least squares or the polynomial curve fitting algorithm by the Newton-Raphson method.

The apparatus 900 is a multiplexed data acquisition and analysis platform for measuring and recording of hybridization and flow cytometric analysis of analyte-antibodies in assays that performs simultaneous measurement of multiple different analytes. The system consists of an array of bioFET cells 261 with a distinct sets of specific probes and the resultant output of the hybridization are addressable by the resident microcontroller 901 interfaced with a digital signal processing board and software. Individual sets of microspheres can be modified with reactive components such as antigens, antibodies, or oligonucleotides, and then mixed to form a multiplexed assay set. The digital signal-processing hardware and software provide complete control of the flow cytometer and perform real-time data processing, allowing multiple independent reactions to be analyzed simultaneously. The system 900 performs qualitative and quantitative immunoassays for multiple serum proteins in both captures. The system can be used to perform DNA sequence analysis by multiplexed competitive hybridization with different sequence-specific oligonucleotide probes.

FIG. 20 is a diagram representing the impedance coverage range 909 as a function of frequency with and without the use of the analog front end (AFE) 904 and direct digital synthesizer (DDS) 903. The impedance converter 902 has limited coverage in terms of frequency range and impedance range, as shown by region A, while region B indicates the expanded lower impedance measurement range provided by the inclusion of the DDS circuit 903, region C indicates the expanded lower frequency range afforded by the incorporation of the AFE circuit 904, and region D represents the fully expanded test frequency range and widened impedance measurement range employing the AFE 904 and DDS 903 together.

Further elaboration of the system 900 operation is noted by following FIG. 19 signal flow, where microcontroller 901 (such as PIC32MX460F512L) is used to direct traffic, CPU (MC) 901 further fetches instructions, decodes each instruction, fetches source operands, executes each instruction and writes the results of instruction execution to the proper destinations. The microcontroller 901 selects via gain multiplexer 906 a cell and compares the outputs of the bioFET sensors 1 (or array 261) with impedance converter 902 (such as AD5933). The AD5933 is a high precision impedance converter system solution that combines an on-board frequency generator with a 12-bit, 1 MSPS, analog-to-digital converter (ADC). The frequency generator allows an external complex impedance to be excited with a known frequency. The response signal from the impedance cell is sampled by the on-board ADC and a discrete Fourier transform (DFT) is processed by an on-board DSP engine. The DFT algorithm returns a real (R) and imaginary (I) dataword at each output frequency. Once calibrated signal is achieved by comparing between biosensor signal cell and biosensor reference cell, the magnitude of the impedance and relative phase of the impedance at each frequency point along the sweep is easily calculated by the arithmetical unit (AU). The DDS 903 unit (such as AD9834) defines the clock traffic within the apparatus 900 with its other functional blocks of the analog front end 904. The bioFET sensor outputs is constantly compared by the saturation detector 907 and enables a selection of the appropriate gain necessary for linearization as shown and described by FIG. 20 with its direct digital synthesizer (DDS), FIG. 21 where the signal undergoes a multi gain stage which increases the impedance range, and FIG. 22 where saturation detection circuit determines the appropriate value to be selected from the gain bank resistor 906.

The benefit of using the external AFE circuit 904 is that it provides reduced output impedance of the signal source, where the impedance converter 902 has output resistance associated with each programmable output voltage (200Ω to 2.4 kΩ), while employing a low-output impedance (<1Ω) source follower amplifier 27 with sufficient bandwidth as a buffer to eliminate the effect of noise on the impedance measurement sampled by the apparatus 900.

To re-bias the excitation signal, each programmable output voltage in impedance converter 902 has a different bias associated with it, and adding high pass filter 908 to remove the DC bias from the transmit stage and re-biasing the AC signal allows the DC bias to be re-centered at midpoint, $V_{dd/2}$. Since the amplifier 910 in FIG. 21 on the receiving path is also DC biased at $V_{dd/2}$, there is zero DC bias applied to the biosensor. This avoids possible thermal damage to the fluid sample (antibody and analyte) due to an applied voltage over a long measurement time.

Since the smallest excitation signal $V_{pp}$=198 mV and $V_{dc}$=173 mV from impedance converter 902 is greater than what the biosensor 1 requires, in one embodiment, op-amps are employed to further attenuate the excitation signal to 40 mV, and to apply proper gain before feeding the signal back to the impedance converter 902. Due to the complex nature of biosensor impedance over wide sweep frequency, the impedance value may be as small as few dozen ohm, and as large as several Mega-ohm. The active circuit 900 is designed to measure impedance from 100Ω to 10 MΩ namely a ratio=10 MΩ/1000=100000.

FIG. 21 is a schematic of partial multi-gain stage post amplifier circuit 910 included in gain multiplexer 906, which is incorporated to solve the wide impedance range problem expressed in FIG. 20, where the impedance range spans from 10 MΩ to 100Ω. This order of magnitude range is achieved by placing a multiple resistor bank 913 as the gain feedback resistor of the post-amplifier 910, using in this example four switched resistors to cover the entire sampling range. The calibration resistor bank 913 is included to provide individual calibration at each gain stage.

FIG. 22 is a schematic of a partial saturation detection circuit 911 included within saturation detection circuit 907, samples the post amplified signal (0 to 3.3 V) provided to the impedance converter 902, and compares it with the high (VrefH=3.15 V) and low (VrefL=0.15 V) thresholds. If the signal is out of the range, the comparator outputs CompH and/or CompL will be high, causing the alarm to be set by the flip-flop 912. The alarm is monitored by the microcontroller 901, and triggers the auto gain selection software module to lower the input amplifier gain in gain multiplexer 906 by selection of an appropriate resistor value in circuit 910 in FIG. 21 which is included in gain multiplexer 906. The microcontroller 901 then clears the alarm by setting the reset pin, CLEAR, high in the flip-flop 912 of circuit 911 in FIG. 22.

FIG. 23 is a flowchart 913 detailing the auto gain selection software logic in microcontroller 901 designed to select the proper post-amplifier gain based on the output of saturation detection circuit 907 to insure the impedance signal within impedance converter 902 is within its linear range. In one embodiment, the embedded software is designed to function as a state machine to control the impedance measurement sequence of impedance converter 902 over output 714, and to further provide control of DDS 903 over output 912.

FIG. 23 further illustrates the methodology of the impedance measurement sequence of circuit detail defining the impedance converter 914. Calibration begins at step 100 followed by configuration of the circuit 902 (impedance converter using e.g. a device such as AD5933) at the first frequency sweep point at step 102. The gain of gain multiplexer 906 is set at its highest gain at step 104. The impedance at the first sweep is then measured at step 106. A determination is made at step 108 whether or not saturation has been achieved. If saturation has been achieved, then the gain of gain multiplexer 906 is set to a lower level at step 110 and the process returns to step 104 for the next series of sweeps. If saturation has not been achieved, then a measurement result is saved by microprocessor 901 at step 112. A determination is then made at step 114 whether or not the frequency sweep just made is the last one to be made in the series or not. If not, then the next frequency sweep point is selected at step 116 and the process returns to step 104. If the frequency sweep made is the last one of the programmed series, then the calibrated magnitude and phase of the impedance is calculated at step 118.

In another embodiment the software provides the communication protocol with the graphic user interface (GUI) 916 over universal serial bus (USB) 917. In another embodiment, the software provides general-purpose input/output (GPIO) control of gain and Z multiplexing. In another embodiment the software provides an alarm in the event of saturation detection.

In another embodiment the software provides variable gain selection, and automatic calibration of the system. The flow diagram depict an impedance converter 903, which is a high precision impedance converter system solution that combines an on-board frequency generator such as for example Analog Devices AD5933 with a 12-bit, 1 MSPS, analog-to-digital converter (ADC). The frequency generator allows an external complex impedance to be excited with a known frequency. The response signal from the impedance measurement is sampled by the on-board ADC and a discrete Fourier transform (DFT) is processed by an on-board digital signal processor DSP engine in converter 903. The DFT algorithm returns a real (R) and imaginary (I) dataword at each output frequency for impedance. Once calibrated, the magnitude of the impedance and relative phase of the impedance at each frequency point along the sweep is calculated. This is done by microcontroller 901 using the real and imaginary register contents, which can be read from the serial I²C interface. The microcontroller 901 commands the gain multiplexer 906 to select the proper resistance value as indicated and described by FIG. 20, if saturation is detected by the circuit 912 defined by FIG. 22 then the microcontroller 901 commands the multi-gain circuit 910 described in FIG. 21 to select the appropriate value, and the measurement is taken and stored. The process is reinitiated upon command from the microcontroller 901.

FIG. 24 depicts a display screen 217 of the graphic user interface (GUI), indicating the various parameters needed to enable the user interface to perform the tasks and display the relevant data and analysis of the bioFET sensor 1. The data mining as well as data reduction and display are noted in examples using MATLAB for a finite state machine, to control and model the bioFET sensor array, can configure and modify the visual and fields of interest on demand. Using finite state machines to model control logic of a reactive system displays a finite set of states and behaviors and how the system transitions from one state to another when certain conditions are true. Examples of operations containing complex impedance measurements, includes scheduling a sequence of tasks or steps for a system defining fault detection, isolation, and recovery logic supervising how to switch between different modes of display and analysis options.

Circuit Modeling of the BioFET Cell

FIG. 25 shows an R/C equivalent circuit of sensor 1 where R 218 and C 221 are in parallel. Where R 218=10 kΩ (9.86 kΩ measured) and the value of C 221=10 nF (9.5 nF measured). Using this equivalent circuit of sensor 1 as exemplified by a prototype fabricated at our laboratory, a set of experiments were conducted in order to validate the modeling of the novel biosensor 1 and it's analog-front-end. The device measured impedance against the sweep frequency from 50 Hz to 100 kHz, indicated a close correlation between data obtained vs. theoretical prediction of the bioFET sensor 1. The data were collected using the developed impedance measurement device, i.e., Pathfinder or Reader of FIG. 9, and the plotted data indicate the observed impedance value against the applied frequency using excel via MATLAB, employing the general expression for impedance of 50 Hz to 100 kHz CPE is as follows:

$$Z_{CPE} = \frac{1}{\omega_0 \cdot V} \cdot \left(\frac{j\omega}{\omega_0}\right)^{-\alpha}$$

Where V is the voltage across the sensor 1, ω is frequency applied to the sensor 1 and $\omega_0$ is the frequency of 50 Hz to 100 kHz. Here, α value is in between 0 (Zcpe becomes entirely resistive) and 1 (Zcpe becomes entirely capacitive). We have seen the alpha range from 0.5 to 0.9 depends on the data set and modeling configuration and the α value changes during the anti-body/antigen conjugating process. In the time domain, a simple exponential curve for the R/C equivalent circuit did not accurately describe the actual circuit equivalence of the sensor 1. The R//C network's impedance is calculated in a excel spread sheet using Matlab. The test data is collected using Pathfinder. The calculated and measured data are plotted against each other in FIG. 26. The graph of FIG. 26 shows the magnitude of the impedance and its corresponding phase change with the applied frequency.

A biosensor 1 was tested to compare the results observed by Pathfinder of FIG. 9 and a commercially available electrochemical impedance spectroscopy (EIS) (Zahner, Model #IM6). Both results are shown in the FIG. 27. The data observed at the frequency range from 3 kHz to 300 kHz. The impedance increases with the decreasing frequency for both cases, which is supported the theoretical model. FIG. 28 is a graph comparing the phase of the impedance as observed by Pathfinder in FIG. 9 and a commercially available electrochemical impedance spectroscopy (Zahner, Model #IM6). The same biosensors 1 were used for both cases.

Analog Computational Unit Included in the Analog Front End

FIG. 30A-30D are schematics of analog operational circuits that may be used in an analog computational analyzer used in the application incorporating the principles of cellular bioFET array, where a parallel computing paradigm similar to neural networks is applied in order to solve the diffusion as well as the hybridization problem for a variety of proteins and DNA captured by the apparatus 900 in a manner in which the cellular biological process-dynamics is mimicked and the underlying protein sequences observed in the sensor 1 is counted and certain arithmetical procedures are applied. It is to be understood that many other analog operational circuits in addition to those shown in FIG. 30A-30D could be included.

Following Shannon, C E. 1941. "Mathematical Theory of the Differential Analyzer." And due to the facts that: analog computation is a better analytical tool-modeling, as it resemble the physical laws and where computation are realized as a continuous function, and where analog circuits often use fewer devices than corresponding digital circuits, for example, a four-quadrant adder (capable of adding two signed numbers) can be fabricated from four transistors, and where two transistors are sufficient to compute the logarithm or exponential, five for the hyperbolic tangent (which is very useful in neural computation), and three for the square root. As discussed herein, an analog computation unit is incorporated to enable the apparatus 900 with its bioFET 1 in a sensor array configuration 261 to generate data stream manipulated by the arithmetical operators such as described by FIG. 30A-30D.

FIG. 30A shows a summing amplifier, FIG. 30B shows a difference amplifier, FIG. 30C shows an integrator and FIG. 30D shows a differentiator. The analog computation devices of FIG. 30A-D employing the bioFET cell unit 1 in an array matrix-configuration are combined and arranged to perform algebraic and integro-differential operations acting upon continuous or analog signals. The high gain D.C. source follower amplifier 27 as exhibited by the configuration of bioFET cell 1, forms the basic operational element of detection. If the passive components in both feedback and input arms are entirely resistive, the circuits of FIG. 30A add the applied voltages in proportion to the ratios of the individual resistors. If the feedback impedance is capacitive, the circuits integrate the sum of the applied voltages, as shown in FIG. 30C. The simplest input and feedback impedances are replaced with complex networks, either passive or active, the amplifier circuit develops more complicated transfer functions than those shown in FIG. 30A-30D, but a general propose analog computer employing a multipliers may be used to form the product of two or more variables. In addition a fixed and variable diode function generators are available to perform various non-linear operations, and a comparator may make elementary decisions based on the value of a particular variable.

The circuit architecture shown in FIG. 32 includes the analog front end 904 coupled between the sensor array 261 of a plurality of sensor and reference cell pairs 801($n$), each pair coupled to a corresponding log amp 8 and filter 908 and through multiplexer 801 to the digital back end including microprocessor 901. The output signal from filter 908 is a continuous analog signal. The apparatus mimics the underlying biological processes employing discrete state spaces, this data is then manipulated by the arithmetical modules (AU) 300 which mathematically describe the physical process operating on time-varying quantities. The analog computational unit 300 and the digital peripherals shown in FIG. 31, record, store and analyze the hybridization as well as the diffusion processes which underlay the biology investigated by the apparatus 900.

FIGS. 31(A), 31(B), 31(C) and 31(D) are schematic diagrams of the arithmetical units (AU) 300 which forms the analog computational apparatus of the bioFET cells 261. The use of carbon nanotube field-effect transistor (s-CNT-FET) as configured in this application is an electronic device for low-power low-voltage digital or analog circuit application. In one of its embodiments, we teach a low-power, low-voltage bioFET's construction with its operational amplifier (OPAMP), forming an analog arithmetic computing circuit, acting as operators in an analog calculator, where the basic building block are: an inverting amplifier, non-inverting amplifier, adder, subtractor, differentiator, and integrator. Example of such an operator acting on the data generated by hybridization is described in FIG. 33.

FIG. 31A is a schematic block diagram describing the interconnection between the sensor array signal output from filters 908 into a universal analog multiplexer 955 including in analog front end 904 in FIG. 31. The multiplexer 955 further enables the selection of the arithmetical operator 914, 915, 916, 917 forming the AU 300. On command from micro-controller 901 the multiplexer 955 enables the command so as to select the desired arithmetical operation within AU 300.

FIG. 33 is a schematic representation of one of optional configurations of connectivity of bioFET 1 (sensor S1 and S2) with the analog arithmetical module (AU) 300. The circuitry is an exemplary demonstration of the multiple configurations by which the bioFET sensor unit 1 can be interfaced with the AU 300. In one embodiment two bioFET sensors 1 are used and are connected to the AU 300 as two inputs. In addition, the AU 300 circuit is fitted with variable gain in the form of the extra FET transistor Q5, where the control transistor bias Q5 changes the gain of the section.

The circuit of FIG. 33 is an illustration of the use of the arithmetical analog calculator in use with the bioFET sensor, comprising of two bioFET sensors are shown as S1 and S2. Both are connected to a voltage amplifier, A1 and A2 respectively. The sensor(s) output two voltages which are proportional to the chemical/biological activity (the hybridization rate of analyte/antibody). These are shown as V1 and V2. These two signals are taken to the inputs of the arithmetical module 300, configured by four FET transistors and are marked as Q1, Q2, Q3 and Q4. The FET Q5 serves as a bias transistor. The four transistors together compute (in this exemplary case) the tan h (hyperbolic tangent) function of the difference between the two input signals, V1 and V2. In addition the AU 300 also computes the derivative of the same function (d/dt of tan h). A simple difference between the two signals is also present. The (AU) 904 outputs are represented as currents, marked as I1, I2 and I3. These currents are proportional to the functions described above. It is necessary to convert these current signals to voltages, hence the addition of the three resistors, R1, R2 and R3. An additional stage of amplification is added to each of the signals after conversion to voltage; indicated as A3, A4 and A5. While considering the energy used in the detection as well as the resulted arithmetical operation, the circuit in FIG. 33 exhibited the substantial saving while performing such operation. The energy budget is in the range of a few femto-amps and it is much more efficient then a digital mathematical computation circuit, when performing similar operation.

In the illustrated embodiment, however, the analog computation unit 300 may provide familiar operations that use differential equations. These include basic arithmetic operations in FIG. 30A-30D, such as algebraic sum 914 and difference 915 ($u(t)=v(t)\pm w(t)$), constant multiplication or scaling ($u(t)=cv(t)$), variable multiplication and division ($u(t)=v(t)w(t)$, $u(t)=v(t)/w(t)$), and inversion ($u(t)=-v(t)$). Transcendental functions may be provided, such as the exponential ($u(t)=\exp v(t)$), logarithm ($u(t)=\ln v(t)$), trigonometric functions ($u(t)=\sin v(t)$, etc.), and further option is the use of a re-solvers for converting between polar and rectangular coordinates. In addition the arithmetical unit 300 perform a definite integration 916 ($u(t)=v_0+\int_{t_0} v(\tau)\,d\tau$), but differentiation may also be provided 917 ($u(t)=.v(t)$).

Reaction-diffusion computation is an important example of continuous-time analog computing within the framework of the apparatus 900, which could be computed in AU 300. In one example the state of the system apparatus 900 with the analyte is represented by a set of time-varying chemical concentration fields, $c_1, \ldots, c_n$. These fields are distributed across a one-, two-, or three-dimensional space $\Omega$, so that, for $x \in \Omega$, $c_k(x, t)$ represents the concentration of chemical (k) at location x and time t. Computation proceeds in continuous time according to reaction-diffusion equations, which have the form: $\partial c/\partial t = D\nabla 2c + F(c)$, where $c=(c_1, \ldots, c_n)^T$ is the vector of concentrations, $D=\text{diag}(d_1, \ldots, d_n)$ is a diagonal matrix of positive diffusion rates, and F is nonlinear vector function that describes how the chemical reactions affect the concentrations.

There are many variations as well as configurations of interfacing the arithmetical unit with the bioFET sensor array 261 and the analog-front-end 904, in one preferred embodiment the analog arithmetic unit 300 and the analog front end 904, function as one integral signal path, to maintain the continuous nature of the signal fidelity, mimicking the underlying cellular biological process in which hybridization and its diffusion coefficient, including its native time constant as well as its impedance value as measured in array 261 are preserved, prior to any digital filtering or smoothing (curve fitting algorithm) the resulting analog signal with its amplified gain and its arithmetical manipulation, is one of the essential embodiments of the proposed apparatus.

If the simple input and feedback impedances are replaced with complex networks, either passive or active, the amplifier circuit will develop more complicated transfer functions than those shown. In addition to the basic amplifiers, the general purpose analog computational unit contains a variety of special purpose units; for example, multipliers to form the product of two or more variables, fixed and variable-diode function generators to perform various nonlinear operations on the variables, switches to start and modify the operations, and comparators to make elementary decisions based on the value of a particular variable. It is the compatibility and simplicity of interconnection of these various components that give the analog computation its flexibility and versatility. An analog computer interface (ACI) is useful in a variety of applications although a digital electronic computer is used in the back-end to process the data. The analog interface is well suited for the solving differential equations (PDE), specifically non-linear differential equations and systems of equations required in mimicking the biological processes. The analog computation unit is comprised of circuits that can perform addition 914, subtraction 915, multiplication, division, integration 916, and differentiation 917, which enable the proposed apparatus 900 to reliably mimic the stochastic-statistical nature of the underlying electrochemical processes which ultimately provide a realistic ground for the biological sequences investigations, as well as the ability to capture and mimic biological processes.

In one of the preferred embodiments of this application, the apparatus and its method solve specific mathematical operations needed in resolving the diffusion equation as well as hybridization of the antibody-analyte conjugate. The mimicking of such biological processes is performed by connecting bioFET cells 1 with analog circuits to record continuous biological processes, in which the hybridization sequencing order in cellular process is replicated in apparatus 900, by employing a suitable memory bank. The data recorded and or analyzed by the resident microcontroller 901 and its associated memory bank can be used as part of the underlying information necessary to understand stochastic hybridization of such biological processes, hence provide a window to the resulting vectorial trends which ultimately contribute to the resulting protein product at the end of the chain in the mimicked cellular process. Inputs to the circuit are voltages which usually vary with time in a prescribed manner and measurement of the output voltage yields the equation's solution as a continuous representation of the effective capacitive loading and its inverse impedance equivalent value.

The method and apparatus proposed by the invention enable the measurement of such process by its ability to capture and analyze the data in the time domain as well as its frequency domain, hence providing for a realistic representation of the underlying biology and its equivalent circuit.

In one embodiment the layout of the circuit and the bioFET cell's position are configured in a manner which enables a measurement of sequence and timing of the hybridization process. Such data of sequencing and time further enable statistical mapping of biological processes.

In other embodiments, data sampling can also be time delayed to allow for sequence processing in the temporal domain. The definition of a system is a collection of independent, interacting entities forming an integrated whole, whose behavior is distinct and qualitatively greater than its parts. Although data samples are specific to individual cells, global patterns in the data can emerge through application of a diffusion algorithm to the data residing in microcontroller 901. In this sense, the analog front interface with its digital processor enables multiple parallel systems of hybridization to be traced, due to their dynamics, and data patterns are derived from the correlation or relationship of data sequences between the different bioFET cell's units in the array 261 by using different antibodies located in different bioFET cell units.

An example for such use is the flow of an analyte sample containing multiple biomarkers (antibodies) 28 and where different bioFET sensors 1 measure and record the hybridizations of two or more of such biomarkers antigens 29 simultaneously. A typical diagnostic procedure which enables the correlation of such, is noted by measuring the presence and densities of multiple biomarker and their respective values such as VEGF165, C-ERBb-2 AND P53 from a patient's sample by obtaining the density matrices of the three biomarkers in one continues dataset, by the use of apparatus 900. The simultaneous hybridization of multiple biomarker is here analyzed as a phase space of multidimensional vectors to enable the resultant data to lead to a statistical correlation of possible causal connection between multiple biomarkers such as: VEGF165, c-ERBb-2 AND p53. A density matrix for a biomarker is thus a matrix that describes a system where different parameters are available at the same time, such as impedance, time and geometrical location of the cell, which enables a recordation of the physical density, location and type of antibody/antigen. This is to be contrasted with a single state vector that describes an assay where multiple analytes are measured. The density matrix is the analogue to probability measure (probability distribution of position and time of hybridization). The classical parameterization of phase space statistics can be used as a tool to represent the hybridization of multiple biomarker simultaneously to enable the resultant data to lead to a statistical correlation of possible causal connection between multiple biomarkers such as: VEGF165, C-ERBb-2 AND P53 as clinically an augmentation of the three biomarkers with a positive vectorial change is statistically significant in determining the presence of e.g. breath cancer.

A density matrix is a matrix that describes a system in a state where different parameters are available at the same time, a measure of several elements within that state (time and geometrical location) within a state enable a recordation of density, location and type of antibody/antigen This should be contrasted with a single state vector that describes an assay where multiple analytes are measured The density matrix is the analogue to probability mea sure (probability distribution of position and time stamps of hybridization) and it is assumed as the measure of phase space in classical statistical mechanics.

To emulate and represent a biological sequencing by state-by-state hybridization an analog computing device of the kind described by the application is needed to enable direct solution of polynomial differential equations (PDEs). In general a PDE solver depends on an analogous physical process, that is, on a process obeying the same class of PDEs that it is intended to solve. For example, in Mills, J. W. (2008). "The nature of the extended analog computer." Physica D: Nonlinear Phenomena 237 (9) (Elsevier). pp. 1235-1256, and following Lee A. Rubel, describe use of analog circuit in mimicking the diffusion of electrons in conductive sheets or solids to solve the diffusion equations. In mimicking "reaction-diffusion" biology, a continuous-time analog computing is a necessary step in preserving the fidelity of the process. The state is represented by a set of time-varying chemical concentration fields, $c_1 \ldots c_n$. These fields are distributed across a one-, two-, or three-dimensional space $\Omega$, so that, for $x$ $\Omega$, $c_k(x, t)$ which represents the concentration of analyte k at location x and time t. Computation proceeds continuously in time according to reaction-diffusion equations, which have the form: $\partial c/\partial t = D \; 2c+F(c)$, where $c=(c1 \ldots cn)T$ is the vector of concentrations, $D=diag(d1, \ldots, dn)$ is a diagonal matrix of positive diffusion rates, and F is nonlinear vector function that describes how the chemical reactions affect the concentrations. The use of the analog module (AU) 904 enable such procedure and realization of the Lee A. Ruble's architecture in addressing the effective solution of PDE and their accuracy (precision), by preserving the actual and realistic underlying biology in a continues form and without the customary digital discrete and filtered data reduction.

A careful review of the embodiments of the invention, demonstrate the ability of the cellular array of bioFET 1 sensors to capture, measure, count and analyze the entire biological process of molecular conjugation, in an analog continuous and reliable fashion to enable the tasks of mimicking computational biology in a novel, effective and were results are consistent with scientific standards.

A Clinical Example for the Use of the Apparatus as a Prognostic Tool.

One of the preferred embodiments for the effective use of the apparatus is to assess the prognostic significance of molecular biomarkers, particularly c-erbB-2 and p53 and VEGF165. Defining molecular abnormalities in breast cancer is an important strategy for early detection, assessment of prognosis, and treatment selection. Evidence is strong that selective biomarkers, including c-erbB-2 and p53, have prognostic significance in breast cancer. Study conducted by Beenken S W, et al "Molecular biomarkers for breast cancer prognosis: co expression of c-erbB-2 and p53. (PubMed 2001 May; 233(5):630-8.) support the application of the novel apparatus 900 as the author conclude that." Three hundred eleven patients were accrued to the Alabama Breast Cancer Project, and paraffin-embedded breast cancer tissues for 90 patients were available for immunohistochemical analysis of molecular biomarkers. Univariate analysis showed nodal status, c-erbB-2 expression, and p53 expression to have prognostic significance. Co expression of c-erbB-2 and p53 was also found to have prognostic significance by the log-rank test. Multivariate analysis showed T stage, nodal status, c-erbB-2 expression, and p53 expression to have independent prognostic significance. These data suggest that c-erbB-2 and p53 expression in breast cancer have prognostic significance. After median follow-up of 16 years, co expression of c-erbB-2 and p53 may have more prognostic significance than traditional prognostic factors such as T stage and nodal status". The use of the apparatus 900 with its ability to enable a label-free detection by hybridizing multiple biomarkers simultaneously without the preparation and technical knowhow of laboratory immunostained sections and Immunohistochemical determination after sectioning, can be achieved by the use of the proposed apparatus and the method we teach in this application. The example of such use is obvious to a man familiar with the art, as a possible layout of the apparatus 900 can be set to contain an array 261 of bioFET 1 with a biomarker such as: c-erbB-2-rabbit antihuman c-erbB-2 oncoprotein and second biomarker: p53-mouse monoclonal antihuman p53 (Both antibodies are produced by DAKO, Carpentaria, Calif.), and where bioFET array for both biomarkers are prepared with its specific antigen (as noted above), and where a serum of a patient is introduced to the microfluidic chamber 600 so as to enable measurement of the hybridization process while setting the normal histological reference within the apparatus lookup tables for comparison or alternatively the reference data point can be set as resistor bank within the apparatus. The application as noted can be expended with variations relating to the number of bioFET 1 cells in the array 261 and with different geometrical lay outs as shown in FIGS. 30 and 7A respectively.

FIG. 31 is a schematic representation of analog front end (AFE) 904 with its analog computational unit 300 (arithmetical module). The analysis and selection of the analog computational module is based on the fundamental laws of noise in gene and protein expression, which set limits on the energy, time, space, molecular count and part-count resources needed to compute at a given level of precision (a biological process of hybridization) including the fact that such process invariably take into accounts the diffusion coefficients of such activity, such as hybridization. The literature and comparative studies conclude that analog computation is significantly more efficient in its use of resources than deterministic digital computation modeling, even at relatively high levels of precision in the cell. Based on this analysis, we conclude that synthetic biology must employ an analog, collective analog, probabilistic and hybrid analog-digital computational approaches. Otherwise, even relatively simple synthetic computations in hybridizing protein, such as addition, (as is it demonstrated by example below), will exceed energy and molecular-count budgets. The application further introduces a method and an exemplary apparatus for efficiently representing analog protein to protein computation in vitro. As noted by the prior art of Synthetic Biology: analog electronic circuits operating with sub-threshold transistors and analog molecular flux in chemical reactions, both obey Boltzmann exponential laws of thermodynamics and are described by similar logarithmic electrochemical potentials. It is to be noted that the basic modeling and verification of the preferred embodiments for this application is the ability of the computational unit (AU) 300 of its apparatus 900 to mimic the underlying biological diffusion and hybridization modeling. This application uses recent work which was conducted in our laboratory and confirmed the use of the invention employing *Escherichia coli* and VEGF molecule by further demonstrating the effective realization of the proposed method and its embodiments.

There are striking similarities between chemical-reaction dynamics and electronic current flow in the sub-threshold regime of transistor operation: electron concentration at the source is analogous to reactant concentration; electron concentration at the drain is analogous to product concentration; forward and reverse current flows in the bioFET transistor are analogous to forward and reverse reaction rates in a chemical reaction; the forward and reverse currents in a bioFET transistor 1 is exponential in voltage differences at its terminals analogous to reaction rates being exponential in the free-energy differences within a chemical reaction; increases in gate voltage lower energy barriers in a transistor increasing current flow analogous to the effects of enzymes or catalysts in chemical reactions that increase reaction rates; and the stochastic of the Poisson shot noise in sub-threshold transistors are analogous to the stochastic of molecular shot noise in reactions.

As shown by FIGS. 1A and 1B and system diagram noted by FIG. 19, where the basic cell unit 1 forming in array configuration 261 and where the bioFET cell 1 is a hybrid of semiconductive substrate and a biological element (antibody) the bioelectronic circuit functions as an analog device. The array of cellular elements form a matrix which enables the matrix to perform as a statistical engine to solve partial differential equations of a kind necessary to address two fundamental problems presented by computational biology: mimicking the diffusion process of the underlying biological activities and the statistical counting of hybridization of protein and analyte in near real time.

The disclosed method for detecting the biological process of protein to protein conjugation while counting and recording it using bioFET cells 1 in an array enables continuous analysis by employing the analog front end (AFE) 904, using its analog computational unit (AU) 904, to measure the density matrix with its time-stamps and location of events with one step.

This process is defined by the embodiments of this application as each of the bioFET cells 1 and its array shown in FIG. 9 with its addressable register via the multiplexer (the universal switch 908) and the general purpose MUX 804. The integration of micro-fluidics chamber 600 combined with its electrical impedance spectroscopy-analog-front-end 904, mimicking the underlying biological processes through its equivalent circuit. The ability of apparatus 900 to account for diffusion rate as well as the hybridization is a feature of the illustrated embodiments.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

I claim:

1. A method comprising:
   detecting a biological process of protein-to-protein conjugation while counting and recording the conjugation using an array of bioFET cells; and
   simultaneously making a continuous time analysis of the conjugation by employing an analog front end and an analog computational unit to measure a density matrix of the conjugation with time-stamps of events.

2. The method of claim 1 where detecting a biological process of protein-to-protein conjugation while counting and recording the conjugation using an array of bioFET cells comprises using a bioFET cell which is a hybrid of semiconductive substrate and a biological element the bioelectronic circuit and which functions as an analog device.

3. The method of claim 1 where simultaneously making a continuous time analysis of the conjugation by employing an analog front end and an analog computational unit to measure a density matrix of the conjugation with time-stamps of events comprises using an array of cellular as a matrix to perform as a statistical engine to solve partial differential equations to mimic diffusion of underlying cellular biological activities and statistical counting of hybridization of protein and analyte in real time.

* * * * *